United States Patent
Nag et al.

(10) Patent No.: US 6,794,401 B2
(45) Date of Patent: Sep. 21, 2004

(54) AMINO ACID PHENOXY ETHERS

(75) Inventors: Bishwajit Nag, Union City, CA (US); Abhijeet Nag, Fremont, CA (US); Debendranath Dey, Fremont, CA (US); Shiv Kumar Agarwal, Chennai (IN)

(73) Assignee: Bexel Pharmaceuticals, Inc., Union City, CA (US)

( * ) Notice: Subject to any disclaimer, the term of this patent is extended or adjusted under 35 U.S.C. 154(b) by 0 days.

(21) Appl. No.: 10/356,113

(22) Filed: Jan. 31, 2003

(65) Prior Publication Data

US 2004/0142991 A1 Jul. 22, 2004

Related U.S. Application Data

(60) Provisional application No. 60/440,772, filed on Jan. 17, 2003.

(51) Int. Cl.[7] .................. A61K 31/425; A61K 31/42; C07D 277/04; C07D 263/04
(52) U.S. Cl. ................... 514/369; 514/376; 548/183; 548/227
(58) Field of Search ................. 514/369, 376; 548/183, 227

(56) References Cited

U.S. PATENT DOCUMENTS

| | | | |
|---|---|---|---|
| 5,166,137 A | 11/1992 | Otterlei et al. | |
| 5,441,971 A * | 8/1995 | Sohda et al. | 514/342 |
| 5,527,546 A | 6/1996 | Penza et al. | |
| 6,004,813 A | 12/1999 | Serlupi-Crescenzi et al. | |
| 6,147,100 A * | 11/2000 | Seno et al. | 514/369 |
| 6,331,633 B1 | 12/2001 | Neogi et al. | |
| 6,552,058 B1 * | 4/2003 | Sohda et al. | 514/376 |
| 6,617,339 B1 * | 9/2003 | Gravestock | 514/340 |
| 6,664,281 B1 * | 12/2003 | Tajima et al. | 514/374 |
| 6,667,328 B2 * | 12/2003 | Yoneda et al. | 514/365 |
| 6,680,387 B2 * | 1/2004 | Druzgala et al. | 548/182 |
| 6,686,475 B2 * | 2/2004 | Hindley | 548/183 |
| 6,699,896 B1 * | 3/2004 | Malamas | 514/374 |
| 6,706,746 B2 * | 3/2004 | Fujita et al. | 514/369 |
| 6,730,687 B1 * | 5/2004 | Miyachi et al. | 514/369 |

FOREIGN PATENT DOCUMENTS

| | | |
|---|---|---|
| EP | 1 148 054 A1 | 10/2001 |
| WO | WO 00/64888 | 11/2000 |
| WO | WO 01/02377 A1 | 1/2001 |

* cited by examiner

*Primary Examiner*—Deborah C. Lambkin
(74) *Attorney, Agent, or Firm*—Beyer Weaver & Thomas, LLP

(57) ABSTRACT

Novel amino acid phenyl ethers are provided which exhibit activity for the treatment of immunological diseases, inflammation, obesity, hyperlipidemia, hypertension, neurological diseases and diabetes.

39 Claims, 9 Drawing Sheets

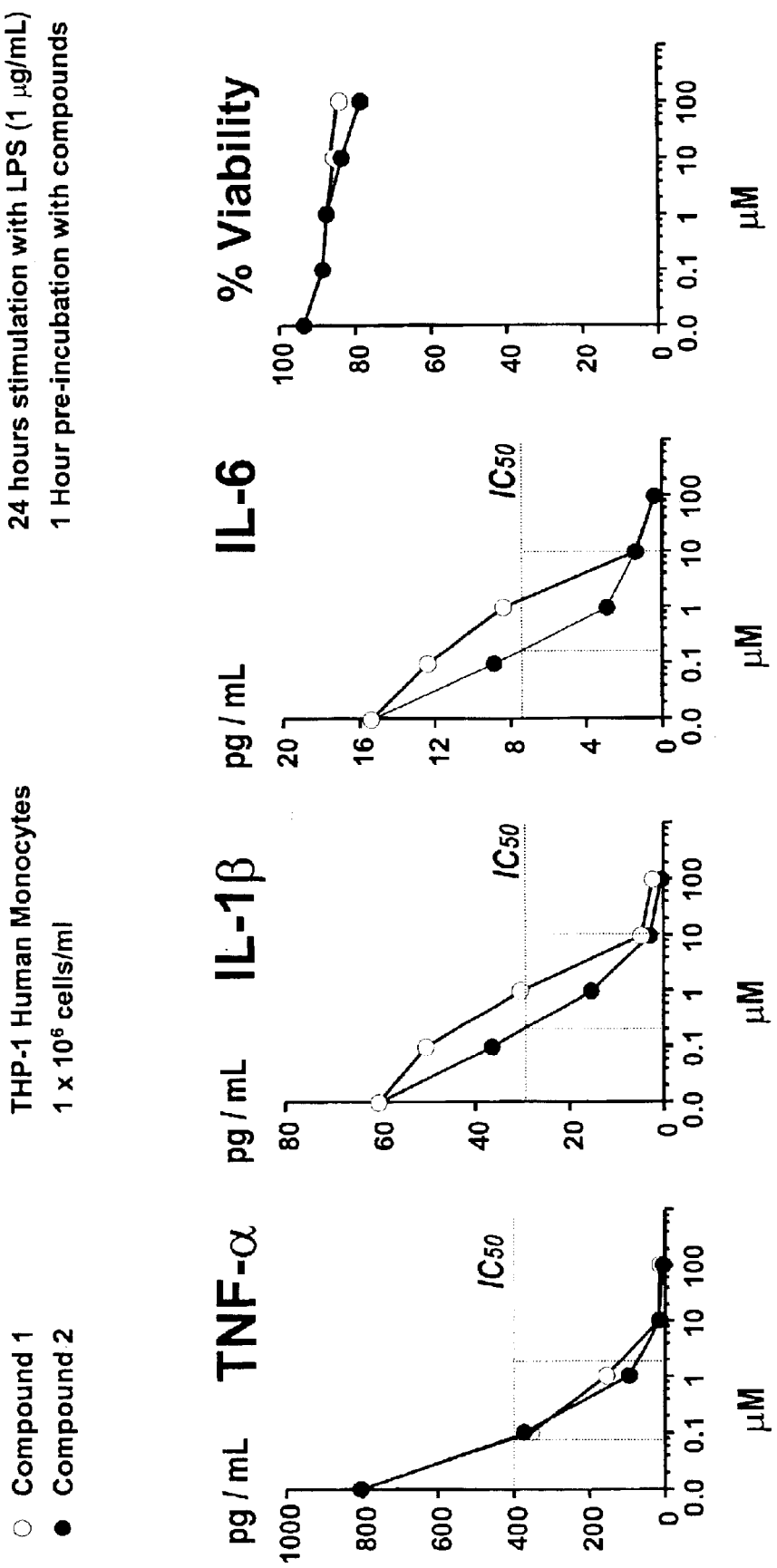
Figure 1: Inhibition of Pro-Inflammatory Cytokines in THP-1 Cells

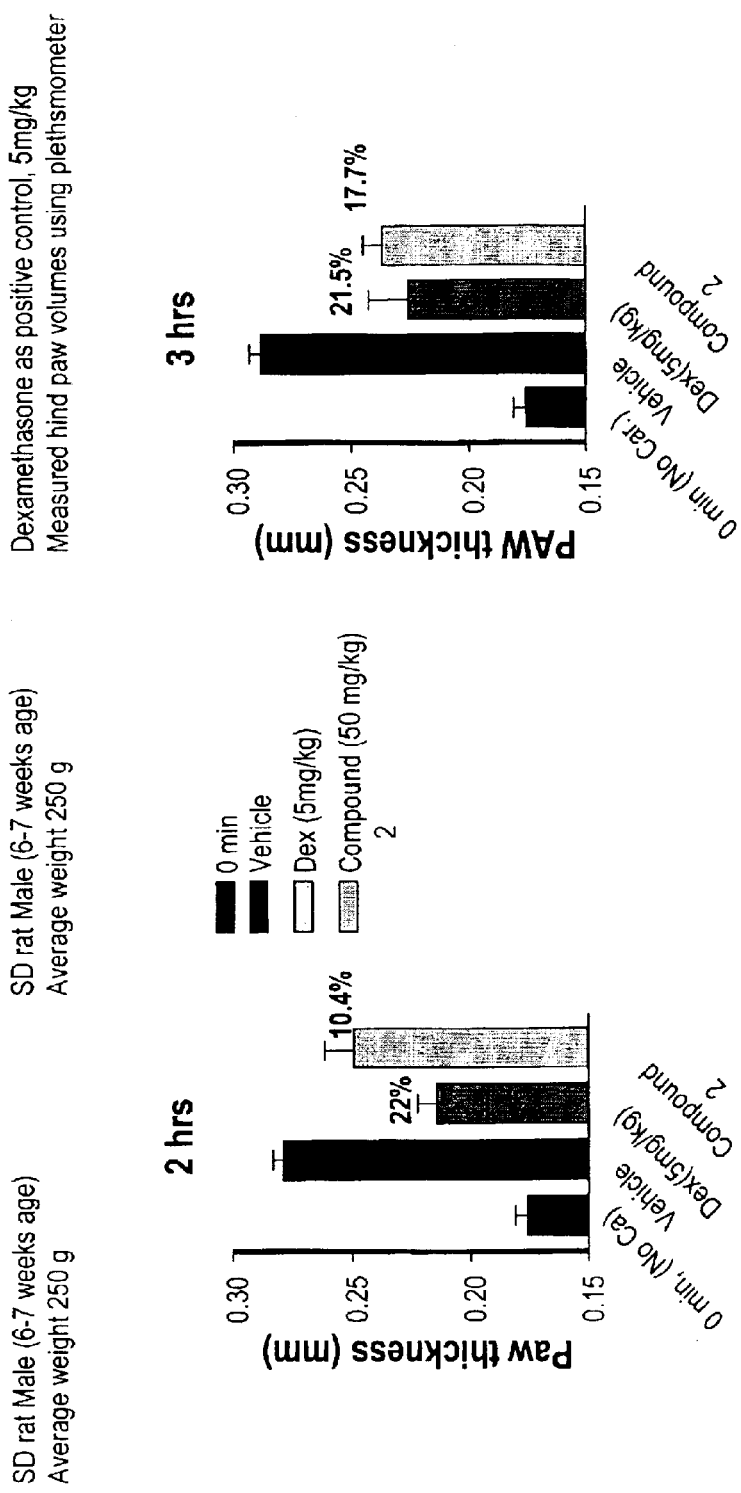
Figure 2. Inhibition of Carrageenan induced PAW edema

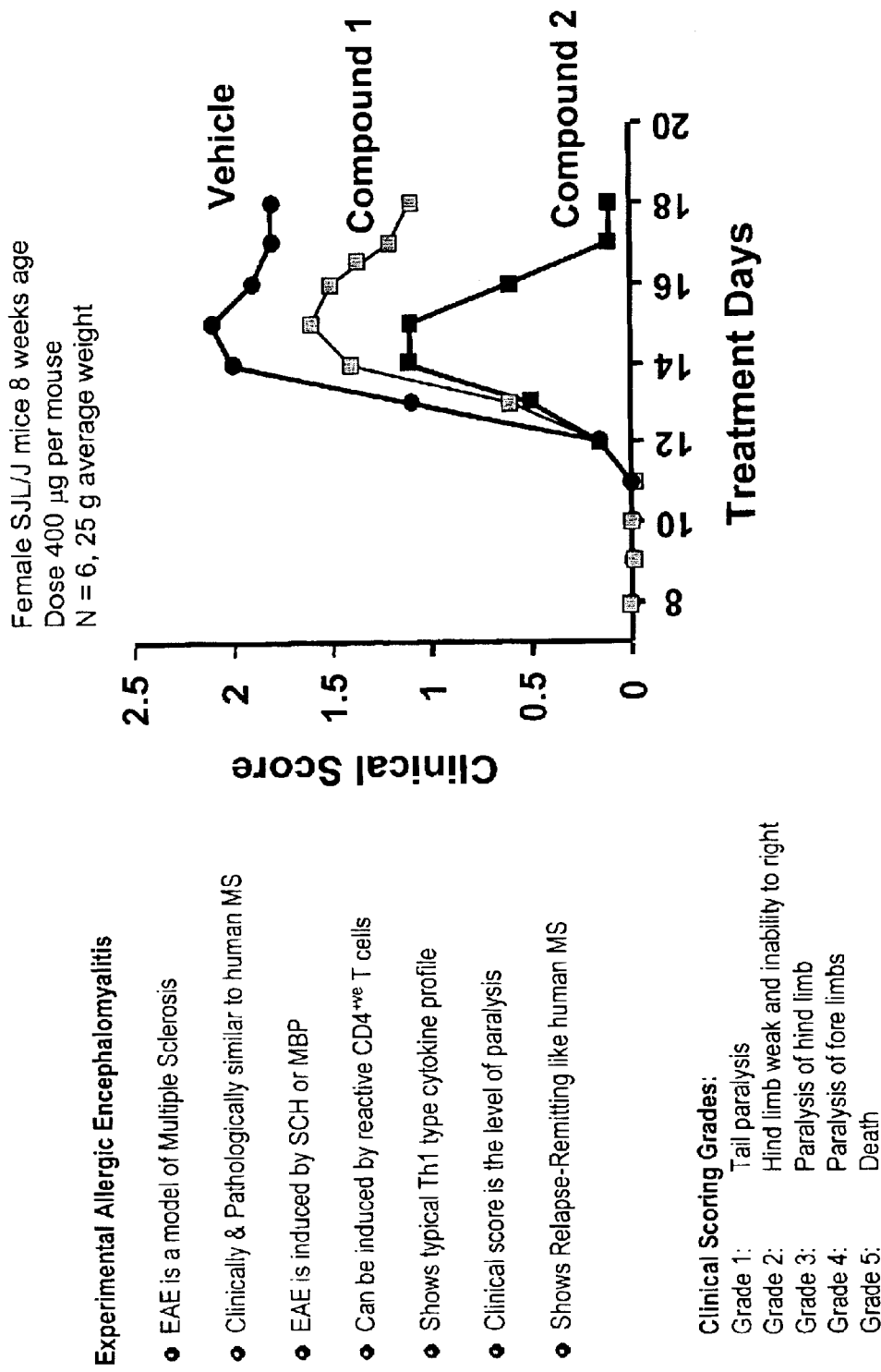

Figure 3. Prevention of EAE in SJL/J Mice

Experimental Allergic Encephalomyalitis

- EAE is a model of Multiple Sclerosis
- Clinically & Pathologically similar to human MS
- EAE is induced by SCH or MBP
- Can be induced by reactive CD4$^{+ve}$ T cells
- Shows typical Th1 type cytokine profile
- Clinical score is the level of paralysis
- Shows Relapse-Remitting like human MS Clinical Scoring Grades:
Grade 1:   Tail paralysis
Grade 2:   Hind limb weak and inability to right
Grade 3:   Paralysis of hind limb
Grade 4:   Paralysis of fore limbs
Grade 5:   Death

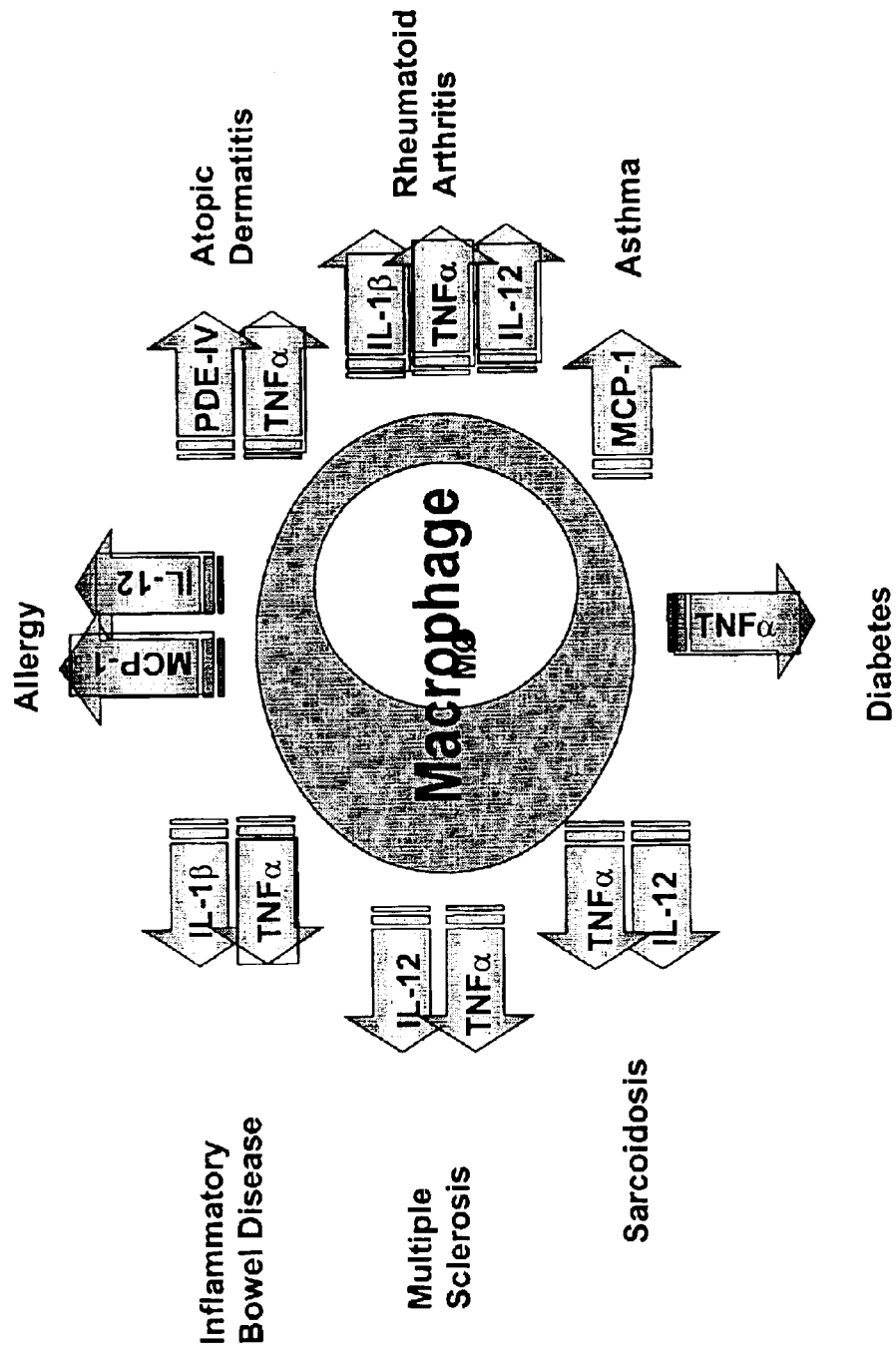
Figure 4. Cytokine modulation in Macrophage & Immune Disorders

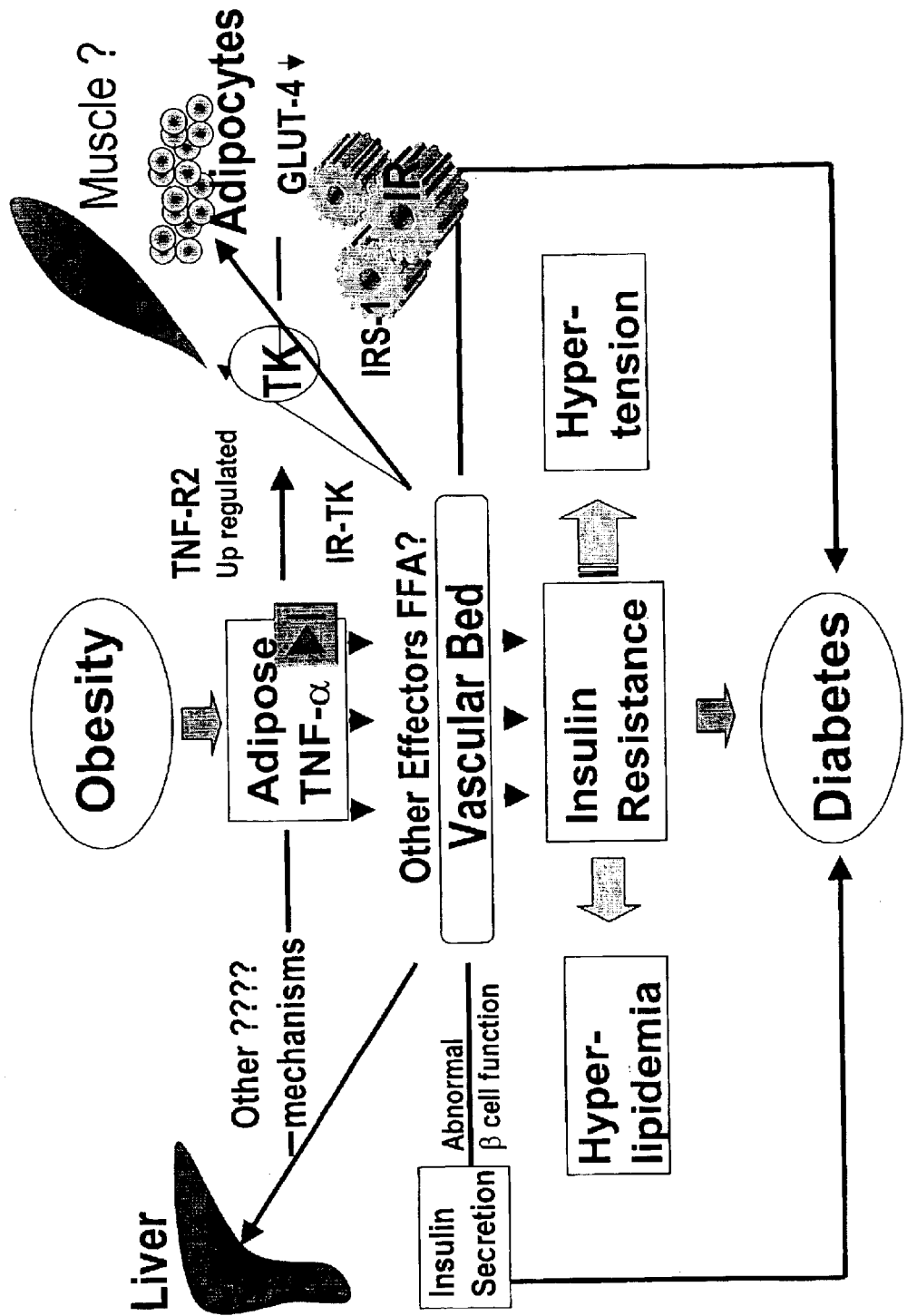
Figure 5. Link of TNFα in Metabolic Disorders

Figure 6. Hypoglycemic activity of Compound 2 in ob/ob and db/db mice
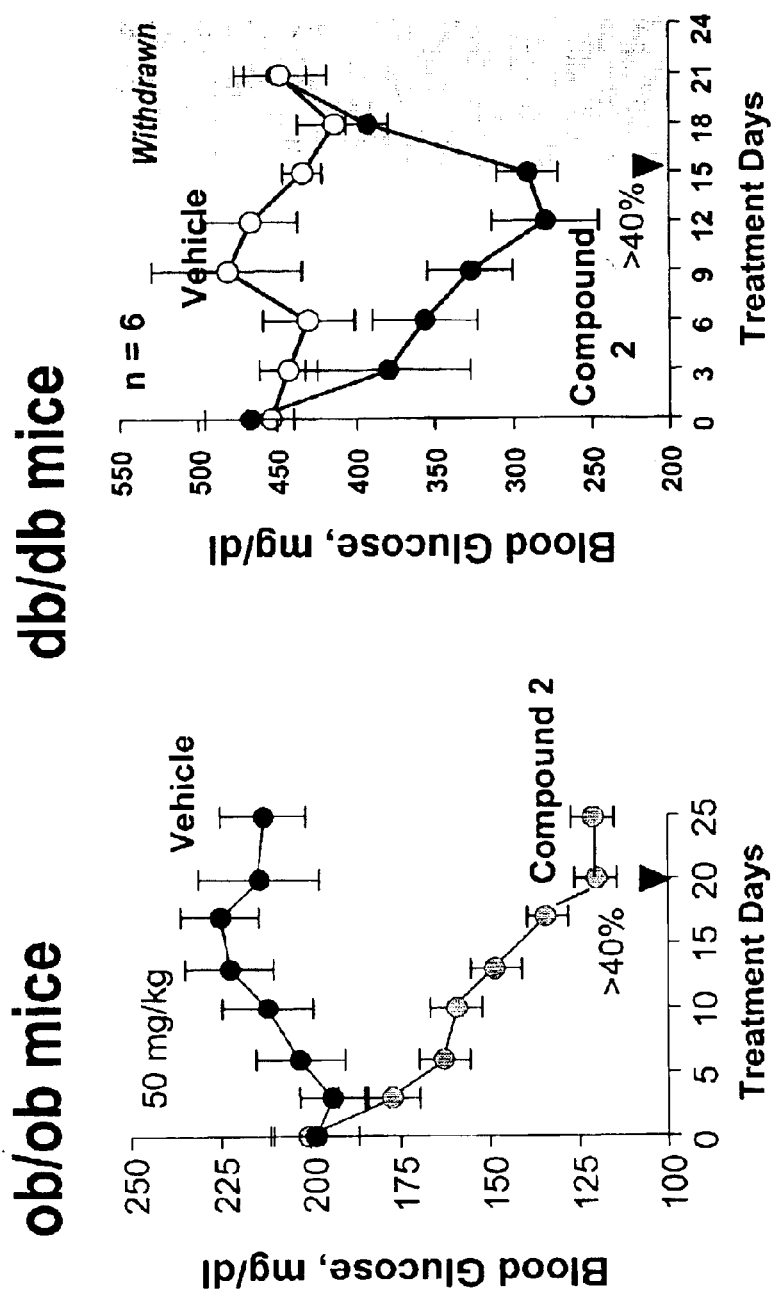

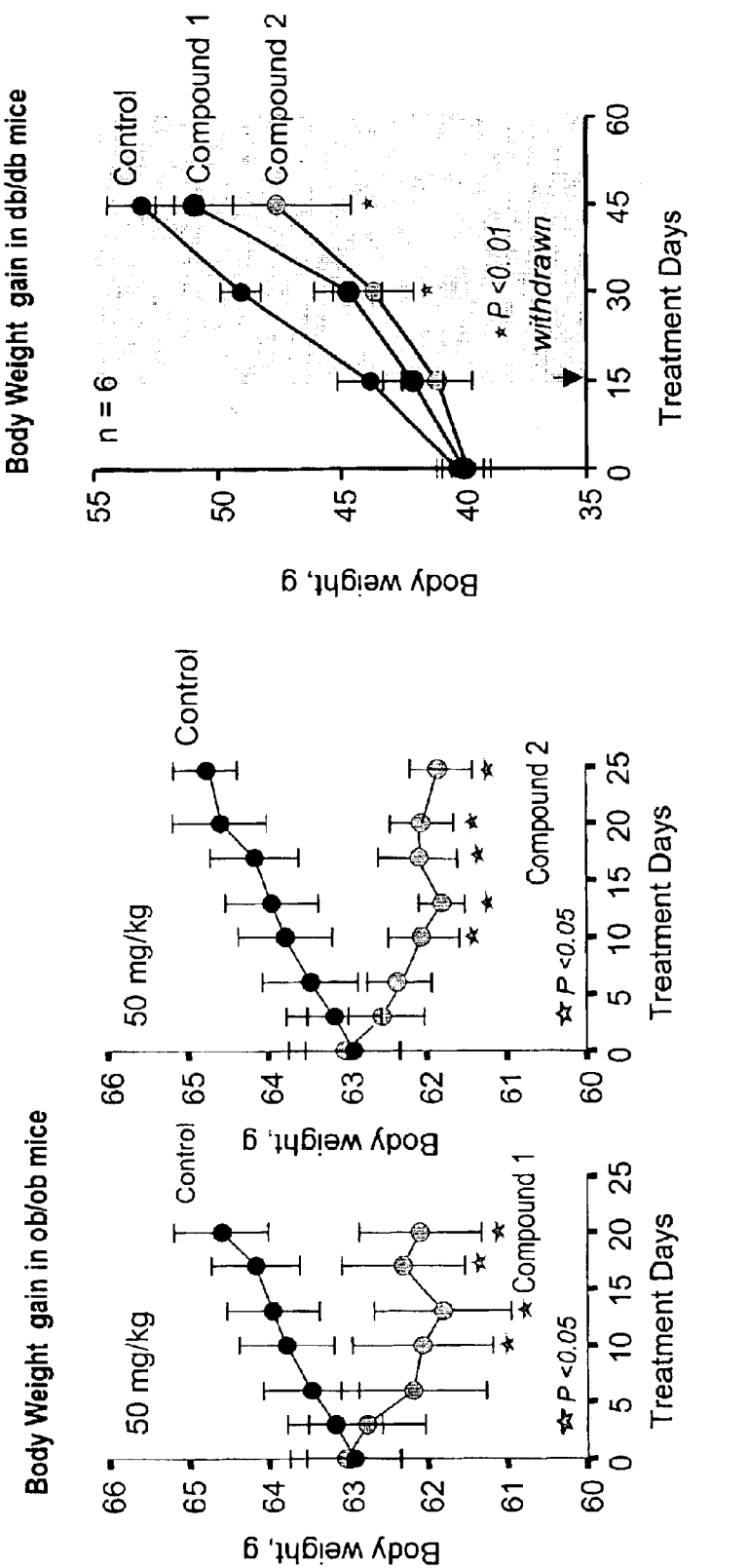
Figure 7. Inhibition of body weight gain increase in obese mice models

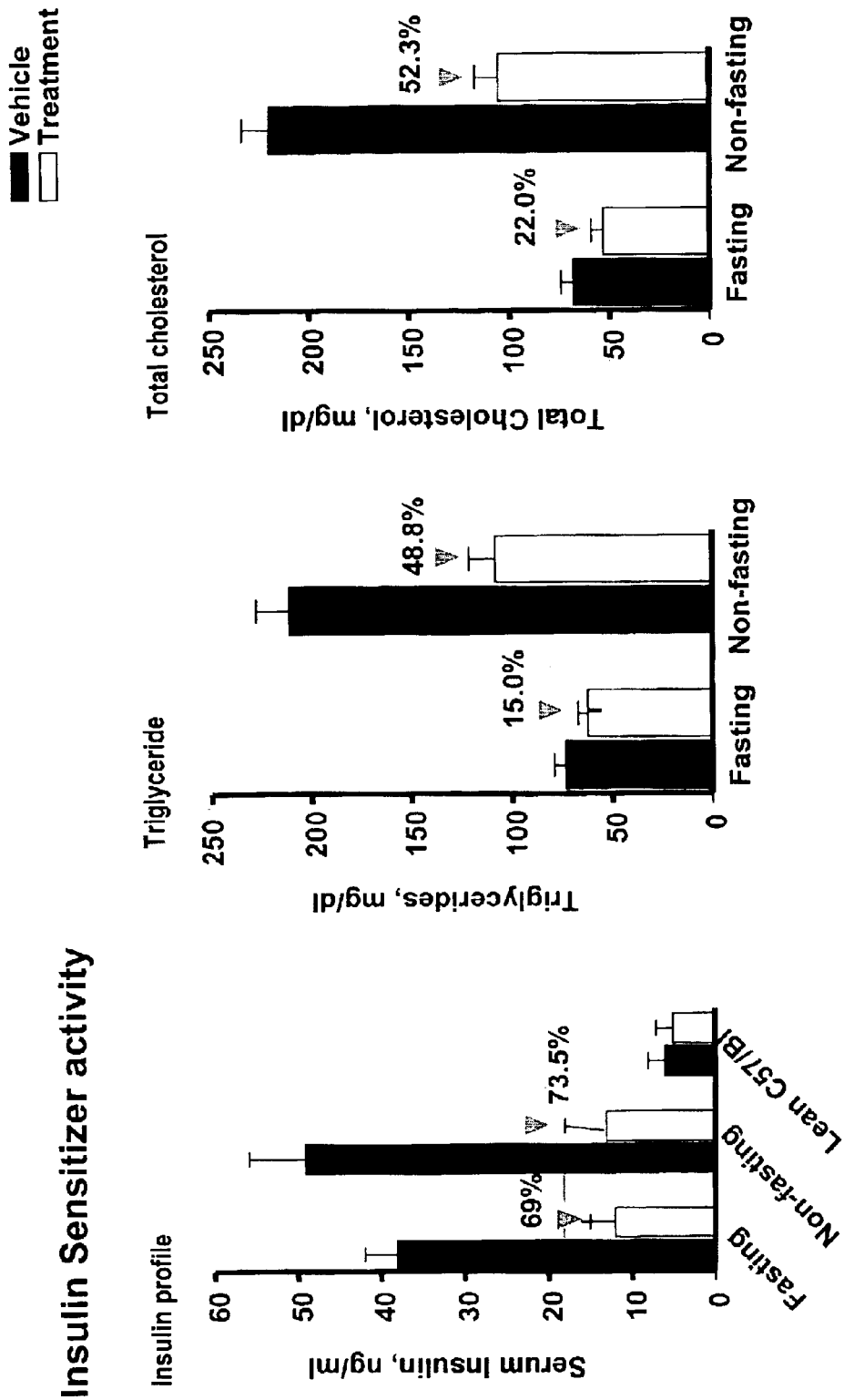
Figure 8. Compound 2 lowers serum insulin, TG and cholesterol in ob/ob Mice

| Compound conc. | OD 1 | OD 2 | OD 3 | Average OD | SD | Corrected Aver. OD | Fold ind. |
|---|---|---|---|---|---|---|---|
| PreAd | 0.091 | 0.074 | 0.078 | 0.081 | 0.009 | -0.014 | |
| Compound 2 0.01uM | 0.141 | 0.125 | 0.123 | 0.130 | 0.010 | 0.035 | 0.80 |
| 0.1uM | 0.129 | 0.134 | 0.130 | 0.131 | 0.003 | 0.036 | 0.83 |
| 1uM | 0.130 | 0.122 | 0.117 | 0.123 | 0.007 | 0.028 | 0.65 |
| 10uM | 0.120 | 0.123 | 0.126 | 0.123 | 0.003 | 0.028 | 0.65 |
| Rosiglitazone 0.01uM | 0.134 | 0.128 | 0.127 | 0.130 | 0.004 | 0.035 | 0.80 |
| 0.1uM | 0.148 | 0.155 | 0.170 | 0.158 | 0.011 | 0.063 | 1.45 |
| 1uM | 0.243 | 0.267 | 0.235 | 0.248 | 0.017 | 0.153 | 3.54 |
| 10uM | 0.290 | 0.275 | 0.311 | 0.292 | 0.018 | 0.197 | 4.55 |
| BRL + TNFa 1uM | 0.162 | 0.151 | 0.139 | 0.151 | 0.012 | 0.056 | 1.28 |
| Vehicle | 0.130 | 0.129 | 0.156 | 0.138 | 0.015 | 0.043 | |
| Blank | 0.108 | 0.089 | 0.088 | 0.095 | 0.011 | 0.000 | |

AMINO ACID PHENOXY ETHERS

This application claims the benefit of the earlier filing date of U.S. Provisional Application No. 60/440,772 filed Jan. 17, 2003, which is incorporated herein by reference.

FIELD OF THE INVENTION

The present invention relates to novel amino acid phenyl ethers for the treatment of immunological diseases, inflammation, obesity, hyperlipidemia, hypertension, neurological diseases and diabetes.

BACKGROUND OF THE INVENTION

The principal elements of the immune system are macrophages or antigen-presenting cells, T cells and B cells. The role of other immune cells such as NK cells, basophils, mast cells and dendritic cells are known, but their role in primary immunologic disorders is uncertain. Macrophages are important mediators of both inflammation and providing the necessary "help" for T cell stimulation and proliferation. Most importantly macrophages make IL 1, IL 12 and TNF-α all of which are potent pro-inflammatory molecules and also provide help for T cells. In addition, activation of macrophages results in the induction of enzymes, such as cyclooxygenase II (COX-2), inducible nitric oxide synthase (iNOS) and production of free radicals capable of damaging normal cells. Many factors activate macrophages, including bacterial products, superantigens and interferon gamma (IFN γ). It is believed that phosphotyrosine kinases (PTKs) and other undefined cellular kinases are involved in the activation process.

Cytokines are molecules secreted by immune cells that are important in mediating immune responses. Cytokine production may lead to the secretion of other cytokines, altered cellular function, cell division or differentiation. Inflammation is the normal response to injury or infection. However, in inflammatory diseases such as rheumatoid arthritis, pathologic inflammatory processes can lead to morbidity and mortality. The cytokine tumor necrosis factor-alpha (TNF-α) plays a central role in the inflammatory response and has been targeted as a point of intervention in inflammatory disease. TNF-α is a polypeptide hormone released by activated macrophages and other cells. At low concentrations, TNF-α participates in the protective inflammatory response by activating leukocytes and promoting their migration to extravascular sites of inflammation (Moser et al., J Clin Invest, 83:444–55, 1989). At higher concentrations, TNF-α can act as a potent pyrogen and induce the production of other pro-inflammatory cytokines (Haworth et al., Eur J Immunol, 21:2575–79, 1991; Brennan et al., Lancet, 2:244–7, 1989). TNF-α also stimulates the synthesis of acute-phase proteins. In rheumatoid arthritis, a chronic and progressive inflammatory disease affecting about 1% of the adult U.S. population, TNF-α mediates the cytokine cascade that leads to joint damage and destruction (Arend et al., Arthritis Rheum, 38:151–60, 1995). Inhibitors of TNF-α, including soluble TNF receptors (etanercept) (Goldenberg, Clin Ther, 21:75–87, 1999) and anti-TNF-α antibody (infliximab) (Luong et al., Ann Pharmacother, 34:743–60, 2000), have recently been approved by the U.S. Food and Drug Administration (FDA) as agents for the treatment of rheumatoid arthritis.

Elevated levels of TNF-α have also been implicated in many other disorders and disease conditions, including cachexia, septic shock syndrome, osteoarthritis, inflammatory bowel disease such as Crohn's disease and ulcerative colitis etc.

Excessive production of IL-6 is implicated in several disease states, it is highly desirable to develop compounds that inhibit IL-6 secretion.

The cytokine IL-1β also participates in the inflammatory response. It stimulates thymocyte proliferation, fibroblast growth factor activity, and the release of prostaglandin from synovial cells.

Elevated or unregulated levels of the cytokine IL-1β have been associated with a number of inflammatory diseases and other disease states, including but not limited to adult respiratory distress syndrome, allergy, Alzheimer's disease etc.

Since overproduction of IL-1β is associated with numerous disease conditions, it is desirable to develop compounds that inhibit the production or activity of IL-1β.

It will be appreciated from the foregoing that, while there have been extensive prior efforts to provide compounds for inhibiting, for example, TNF-α, IL-1, IL-6, COX-2 or other agents considered responsible for immune response, inflammation or inflammatory diseases, e.g. arthritis, there still remains a need for new and improved compounds for effectively treating or inhibiting such diseases.

There appears to be a correlation of TNF-α to adipogenesis (obesity) and other metabolic disorders such as diabetes mellitus. Although, in the past two decades there has been an explosive increase in number of people diagnosed with diabetes worldwide [Amos A., McCarty, D., Zimmet, P. (1997) Diabetic Med. 14, S1–S85; King, H., Aubert, R., Herman, W. (1998) Diabetes Care, 21, 1414–1431], there has been relatively little development of new therapeutics for the treatment of diabetes and its associated conditions [Moller, D. E. (2001) Nature 414, 821–827]. Diabetes exists in two types: insulin dependent Type-I and non-Insulin dependent (insulin-resistant) Type-I. Type-II insulin-resistant diabetes mellitus accounts for 90–95% of all diabetes. This syndromic metabolic disorder currently affects more than 150 million people worldwide and is projected to grow to 300 million by year 2005 [Amos, A., McCarty, D., Zimmet, P. (1997) Diabetic Med. 14, S1–S85; Kopelman, P. G. Hitaman, G. A. (1998) Lancet, 352, SIV5). The main force driving this increase in incidence of type II diabetes is an increase in obesity, the single most important contribution to the pathogenesis of type II diabetes [Kopelman, P. G., Hitaman, G. A. (1998) Lancet, 352, SIV5].

At present, therapy for type II diabetes relies mainly on several approaches intended to reduce the hyperglycemia itself. These are: sulfonylureas and related insulin secretogens that are known to release more insulin from pancreatic β cells; metformin, that acts to reduce hepatic glucose production; peroxisome proliferator-activated receptor (PPAR) agonists that enhances insulin action; a-glucosidase inhibitors that slow down absorption of glucose from the gut; and insulin itself, that suppresses glucose production and augments glucose utilization (summarized in table I below). All of these therapies have limited efficacy, limited tolerability and significant mechanism-based side effects. Of particular concern is the tendency for most treatment to enhance body weight gain. Several current treatments for type II diabetes are associated with episodes of hypoglycemia, and few of the available therapies adequately address underlying defects such as obesity and a phenomenon known as insulin resistance. Among these oral medications, sulfonylureas represent the oldest and widely used form of treatment. Many patients who respond to sulfonylureas initially become refractory to the treatment over time (secondary failure). Besides glucose level and obesity, type II diabetes is now linked with high level of triglycerides and cholesterol. Therefore, there is a need for new classes of drugs addressing the underlying issue of metabolic defects (increasingly known as Syndrome-X) such as obesity, hyperglycemia and hyperlipidemic conditions to address type II diabetes and its associated condition.

TABLE 1

Current Therapeutic agents for Type II Diabetes

| Drug class | Delivery | Molecular | Target Site of Action | Adverse Events |
|---|---|---|---|---|
| Insulin | Intramuscular | Insulin receptor | Liver, Muscle, Fat | Weight gain Hypoglycemia |
| Sulfonylureas (glibenclamide) (repaglinide) (nateglinide) | Oral | SU receptors K+/ATP channel | Pancreatic β cells | Weight gain Hypoglycemia |
| Metformin (biguanides) | Oral | Unknown | Liver (muscle) | GI disturbance Lactic acidosis |
| α-Glucosidase Inhibitors (Acarbose) | Oral | α-Glucosidase | Intestine | GI disturbance |
| PPAR-agonist (Rosiglitazone) (Pioglitazone) | Oral | PPAR-gamma | Fat, Muscle, Liver | Weight gain Anaemia Oedema |

SUMMARY OF THE INVENTION

The present invention, relates to novel amino acid phenyl ethers of formula (I)

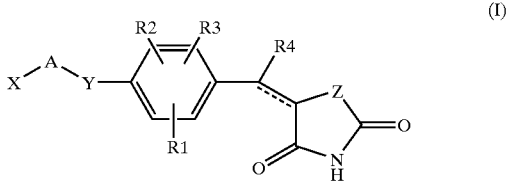

their derivatives, their analogs, their tautomeric forms, their stereoisomers, their polymorphs, their pharmaceutically acceptable salts, their pharmaceutically acceptable solvates, wherein - - - represents optional double bond; Y represents oxygen, sulfur or NR, wherein R represents hydrogen or alkyl; Z represents oxygen or sulfur; $R_1$, $R_2$, $R_3$ and $R_4$ may be same or different and independently represent hydrogen, halogen, hydroxy, nitro, cyano, formyl, amino, alkyl, alkoxy group; A represents a bond or substituted or unsubstituted aryl, heterocyclyl or heteroaryl ring; X represents an alpha amino carboxylic acid or its derivatives bonded to A or Y through its alpha side chain.

The present invention also relates to a process for the preparation of the above said novel compounds, their analogs, their derivatives, their tautomeric forms, their stereoisomers, their polymorphs, their pharmaceutically acceptable salts, pharmaceutically acceptable solvates, novel intermediates and pharmaceutical compositions containing them. Tautomeric forms are isomeric forms which exists in a state of equilibrium capable of reacting according to either form. Stereoisomers include configurational isomers, such as cis- and trans-double bonds, as well as optically active isomers having different spatial arrangements of their atoms. Polymorphs are molecules which can crystallize in two or more forms. Solvates are molecular or ionic complexes of molecules or ions of solvent with those of a solute. An alpha-amino carboxylic acid includes, but is not limited to, naturally-occurring amino acids. The alpha side chain is a group, including hydrogen, covalently bonded to the alpha carbon of an alpha-amino carboxylic acid. Analogs include those compounds which differ by substitution of an oxygen, sulfur, nitrogen or carbon atom in place of such an atom. Analogs also include atoms of the same family of the Periodic Table, such as F, Cl, Br, I, As. Derivatives include compounds resulting from routine functionalizing of atoms, such as, derivatives found by protecting amino or carboxyl groups by carboxylation or esterification, respectively.

The compounds of the present invention are effective in lowering blood glucose, serum insulin, free fatty acids, cholesterol and triglyceride levels and are useful in the treatment and/or prophylaxis of diabetes. The compounds of the present invention are effective in treatment of obesity, inflammation, autoimmune diseases such as such as multiple sclerosis and rheumatoid arthritis. Surprisingly, these compounds increase the leptin level and have no liver toxicity.

Furthermore, the compounds of the present invention are useful for the treatment of disorders associated with insulin resistance, such as polycystic ovary syndrome, as well as hyperlipidemia, coronary artery disease and peripheral vascular disease, and for the treatment of inflammation and immunological diseases, particularly those mediated by cytokines such as TNF-α, IL-1, IL-6, IL-1β and cyclooxygenase such as COX-2.

BRIEF DESCRIPTION OF FIGURES

FIG. 1 shows that the compounds in Example 1 lower pro-inflammatory cytokines in human macrophage cells.

FIG. 2 shows efficacy of compound 2 in Example 1 in an animal model of inflammation.

FIG. 3 shows efficacy of compounds 1 and 2 in Example 1 in an animal model of autoimmunity.

FIG. 4 represents schematic illustration of various cytokines and their role in management of a number of inflammatory and autoimmune diseases.

FIG. 5 is a schematic illustration of how TNFα is linked to various metabolic disorders besides its inflammatory and autoimmune properties.

FIG. 6 shows the blood glucose lowering effect of compound in Example 1 in ob/ob and db/db mice.

FIG. 7 shows the effect of compounds 1 and 2 in Example 1 in weight gain reduction in an animal model of obesity.

FIG. 8 shows the effect of compound 2 in Example 1 an insulin sensitizing and lipid lowering activity.

DETAILED DESCRIPTION OF THE INVENTION

Figure 9:
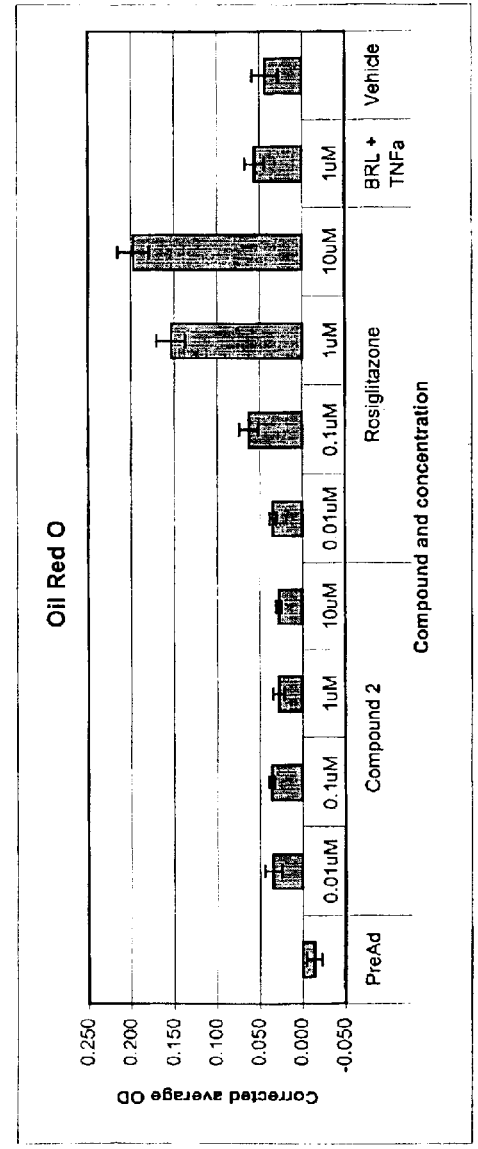
FIG. 9 shows the effect of lipid accumulation in human preadipocytes when treated with various dosages of a compound of the invention compared to rosiglitazone.

In an embodiment of the present invention, the groups represented by $R_1$, $R_2$, $R_3$ and $R_4$ are selected from hydrogen, halogen such as fluorine, chlorine, bromine or iodine; hydroxy, nitro, cyano, formyl, amino, linear or branched, substituted or unsubstituted ($C_1$–$C_{12}$)alkyl group such as methyl, ethyl, propyl, isopropyl, n-butyl, isobutyl, t-butyl, pentyl, hexyl, octyl, nonyl and the like; substituted or unsubstituted ($C_1$–$C_{12}$)alkoxy group such as methoxy, ethoxy, propoxy, butoxy and the like.

In an embodiment of the present invention, the group represented by A is selected from aryl such as phenyl, naphthyl, and the like; heteroaryl ring such as pyridyl, pyrrolyl, thiazolyl, indolyl, imidazolyl, furyl and the like; heterocyclyl ring such as piperzine, morpholine, piperidine, pyrrolidine and the like. The group A may be mono, di or tri substituted and the substituents are selected from halogen, hydroxy, nitro, cyano, formyl, amino, alkyl, haloalkyl, alkoxy, haloalkoxy and the like.

In an embodiment of the present invention, the amino acid and side chain represented by X, X-A or X-A-Y is selected from alanine, glycine, arginine, asparagine, cysteine, glutamic acid, glutamine, histidine, isoleucine, leucine, lysine, methionine, ornithine, proline, serine, threonine, tryptophan, tyrosine and the like, which may be substituted or unsubstituted and their derivatives such as ester and amides of carboxylic acid. The preferred substituents are selected from halogen, alkyl, alkoxy, aryl, heteroaryl, amino and the like.

The amino acid X-A-Y preferably represents substituted or unsubstituted arginine, asparagine, cysteine, glutamine, histidine, lysine, methionine, ornithine, proline, serine, threonine, tryptophan, tyrosine and their derivatives. The group X-A also preferably represents alanine, glycine, isoleucine, leucine and their derivatives. In another embodiment A represents a substituted or unsubstituted alkyl, heterocyclyl or heteroaryl ring.

In another embodiment, Z is sulfur and Y is oxygen. Preferably, R, through $R_4$ are hydrogen.

Pharmaceutically acceptable salts forming part of this invention include base addition salts such as alkali metal salts like Li, Na, and K salts, alkaline earth metal salts like Ca and Mg salts, salts of organic bases such as lysine, arginine, guanidine, diethanolamine, choline and the like, ammonium or substituted ammonium salts. Salts may include acid addition salts which are, sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, ketoglutarates and the like. Pharmaceutically acceptable solvates may be hydrates or comprising other solvents of crystallization such as alcohols.

Preferably, the present invention relates to novel amino acid phenyl ethers of formula

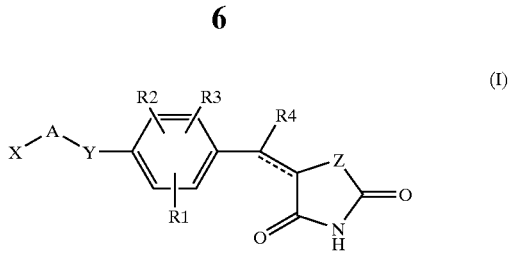

(I)

their derivatives, their analogs, their tautomeric forms, their stereoisomers, their polymorphs, their pharmaceutically acceptable salts, their pharmaceutically acceptable solvates, wherein - - - represents optional double bond; Y represents oxygen, sulfur or NR, wherein R represents hydrogen or alkyl; Z represents oxygen or sulfur; $R_1$, $R_2$, $R_3$ and $R_4$ may be same or different and independently represent hydrogen, halogen, hydroxy, nitro, cyano, formyl, amino, alkyl, or alkoxy; A represents substituted or unsubstituted aryl; X represents an alpha amino carboxylic acid or its derivatives bonded through its alpha side chain to A.

More preferably, the present invention relates to novel amino acid phenyl ethers of formula (I)

their derivatives, their analogs, their tautomeric forms, their stereoisomers, their polymorphs, their pharmaceutically acceptable salts, their pharmaceutically acceptable solvates, wherein - - - represents optional double bond; Y represents oxygen, sulfur or NR, wherein R represents hydrogen or alkyl; Z represents oxygen or sulfur; $R_1$, $R_2$, $R_3$ and $R_4$ may be same or different and independently represent hydrogen, halogen, hydroxy, nitro, cyano, formyl, amino, alkyl, or alkoxy; A represents substituted or unsubstituted phenyl; X represents alanine or its derivatives bonded to A through its alpha methyl group.

Particularly useful compounds according to the invention include:
5-[4-(4-(2-Amino-2-carboxyethyl)phenoxy)benzilidene] thiazolidin-2,4-dione or its salts;
5-[4-(4-(2-Amino-2-methoxycarbonylethyl)phenoxy) benzilidene]thiazolidin-2,4-dione or its salts;
5-[4-(4-(2-Amino-2-carboxyethyl)phenoxy)benzyl] thiazolidin-2,4-dione or its salts;
5-[4-(4-(2-Amino-2-methoxycarbonylethyl)phenoxy) benzyl]thiazolidin-2,4-dione or its salts;
5-[4-(4-(2-Amino-2-carboxyethyl)phenoxy)benzilidene] oxazolidin-2,4-dione or its salts;
5-[4-(4-(2-Amino-2-methoxycarbonylethyl)phenoxy) benzilidene]oxazolidin-2,4-dione or its salts;
5-[4-(4-(2-Amino-2-carboxyethyl)phenoxy)benzyl] oxazolidin-2,4-dione or its salts;
5-[4-(4-(2-Amino-2-methoxycarbonylethyl)phenoxy) benzyl]oxazolidin-2,4-dione or its salts;
5-[4-(4-(2-Amino-2-carboxyethyl)phenoxy)-2,6-difluorobenzilidene]oxazolidin-2,4-dione or its salts;
5-[4-(4-(2-Amino-2-methoxycarbonylethyl)phenoxy)-2,6-difluorobenzilidene]oxazolidin-2,4-dione or its salts;
5-[4-(4-(2-Amino-2-carboxyethyl)phenoxy)-2,6difluorobenzyl]oxazolidin-2,4-dione or its salts;
5-[4-(4-(2-Amino-2-methoxycarbonylethyl)phenoxy)-2,6-difluorobenzyl]oxazolidin-2,4-dione or its salts;
5-[4-(4-(2-Amino-2-carboxyethyl)phenoxy)-2,6-difluorobenzilidene]thiazolidin-2,4-dione or its salts;
5-[4-(4-(2-Amino-2-methoxycarbonylethyl)phenoxy)-2,6-difluorobenzilidene]thiazolidin-2,4-dione or its salts;
5-[4-(4-(2-Amino-2-carboxyethyl)phenoxy)-2,6-difluorobenzyl]thiazolidin-2,4-dione or its salts;
5-[4-(4-(2-Amino-2-methoxycarbonylethyl)phenoxy)-2,6-difluorobenzyl]thiazolidin-2,4-dione or its salts;
5-[4-(4-(2-Amino-2-carboxyethyl)phenoxy)-2,3-difluorobenzilidene]thiazolidin-2,4-dione or its salts;
5-[4-(4-(2-Amino-2-methoxycarbonylethyl)phenoxy)-2,3-difluorobenzilidene]thiazolidin-2,4-dione or its salts;
5-[4-(4-(2-Amino-2-carboxyethyl)phenoxy)-2,3-difluorobenzyl]thiazolidin-2,4-dione or its salts;
5-[4-(4-(2-Amino-2-methoxycarbonylethyl)phenoxy)-2,3-difluorobenzyl]thiazolidin-2,4-dione or its salts;
5-[4-(4-(2-Amino-2-carboxyethyl)phenoxy)-2,3-difluorobenzilidene]oxazolidin-2,4-dione or its salts;
5-[4-(4-(2-Amino-2-methoxycarbonylethyl)phenoxy)-2,3-difluorobenzilidene]oxazolidin-2,4-dione or its salts;
5-[4-(4-(2-Amino-2-carboxyethyl)phenoxy)-2,3-difluorobenzyl]oxazolidin-2,4-dione or its salts;

5-[4-(4-(2-Amino-2-methoxycarbonylethyl)phenoxy)-2,3-difluorobenzyl]oxazolidin-2,4-dione or its salts;
5-[4-(4-(2-Amino-2-carboxyethyl)phenoxy)-3-methylbenzilidene]oxazolidin-2,4-dione or its salts;
5-[4-(4-(2-Amino-2-methoxycarbonylethyl)phenoxy)-3-methylbenzilidene]oxazolidin-2,4-dione or its salts;
5-[4-(4-(2-Amino-2-carboxyethyl)phenoxy)-3-methylbenzyl]oxazolidin-2,4-dione or its salts;
5-[4-(4-(2-Amino-2-methoxycarbonylethyl)phenoxy)-3-methylbenzyl]oxazolidin-2,4-dione or its salts;
5-[4-(4-(2-Amino-2-carboxyethyl)phenoxy)-3-methylbenzilidene]thiazolidin-2,4-dione or its salts;
5-[4-(4-(2-Amino-2-methoxycarbonylethyl)phenoxy)-3-methylbenzilidene]thiazolidin-2,4-dione or its salts;
5-[4-(4-(2-Amino-2-carboxyethyl)phenoxy)-3-methylbenzyl]thiazolidin-2,4-dione or its salts;
5-[4-(4-(2-Amino-2-methoxycarbonylethyl)phenoxy)-3-methylbenzyl]thiazolidin-2,4-dione or its salts;
5-[4-(4-(2-Amino-2-carboxyethyl)phenoxy)-3-nitrobenzilidene]thiazolidin-2,4-dione or its salts;
5-[4-(4-(2-Amino-2-methoxycarbonylethyl)phenoxy)-3-nitrobenzilidene]thiazolidin-2,4-dione or its salts;
5-[4-(4-(2-Amino-2-carboxyethyl)phenoxy)-3-nitrobenzyl]thiazolidin-2,4-dione or its salts;
5-[4-(4-(2-Amino-2-methoxycarbonylethyl)phenoxy)-3-nitrobenzyl]thiazolidin-2,4-dione or its salts;
5-[4-(4-(2-Amino-2-carboxyethyl)phenoxy)-3-nitrobenzilidene]oxazolidin-2,4-dione or its salts;
5-[4-(4-(2-Amino-2-methoxycarbonylethyl)phenoxy)-3-nitrobenzilidene]oxazolidin-2,4-dione or its salts;
5-[4-(4-(2-Amino-2carboxyethyl)phenoxy)-3-nitrobenzyl]oxazolidin-2,4-dione or its salts;
5-[4-(4-(2-Amino-2-methoxycarbonylethyl)phenoxy)-3-nitrobenzyl]oxazolidin-2,4-dione or its salts;
5-[4-(4-(2-Amino-2-carboxyethyl)phenoxy)-3-aminobenzilidene]thiazolidin-2,4-dione or its salts;
5-[4-(4-(2-Amino-2-methoxycarbonylethyl)phenoxy)-3-aminobenzilidene]thiazolidin-2,4-dione or its salts;
5-[4-(4-(2-Amino-2-carboxyethyl)phenoxy)-3-aminobenzyl]thiazolidin-2,4-dione or its salts;
5-[4-(4-(2-Amino-2-methoxycarbonylethyl)phenoxy)-3-aminobenzyl]thiazolidin-2,4-dione or its salts;
5-[4-(4-(2-Amino-2-carboxyethyl)phenoxy)-3-aminobenzilidene]oxazolidin-2,4-dione or its salts;
5-[4-(4-(2-Amino-2-methoxycarbonylethyl)phenoxy)-3-aminobenzilidene]oxazolidin-2,4-dione or its salts;
5-[4-(4-(2-Amino-2-carboxyethyl)phenoxy)-3-aminobenzyl]oxazolidin-2,4-dione or its salts;
5-[4-(4-(2-Amino-2-methoxycarbonylethyl)phenoxy)-3-aminobenzyl]oxazolidin-2,4-dione or its salts;
5-[4-(4-(2-Amino-2-carboxyethyl)phenoxy)-2-fluorobenzilidene]thiazolidin-2,4-dione or its salts;
5-[4-(4-(2-Amino-2-methoxycarbonylethyl)phenoxy)-2-fluorobenzilidene]thiazolidin-2,4-dione or its salts;
5-[4-(4-(2-Amino-2-carboxyethyl)phenoxy)-2-fluorobenzyl]thiazolidin-2,4-dione or its salts;
5-[4-(4-(2-Amino-2-methoxycarbonylethyl)phenoxy)-2-fluorobenzyl]thiazolidin-2,4-dione or its salts;
5-[4-(4-(2-Amino-2-carboxyethyl)phenoxy)-2-fluorobenzilidene]oxazolidin-2,4-dione or its salts;
5-[4-(4-(2-Amino-2-methoxycarbonylethyl)phenoxy)-2-fluorobenzilidene]oxazolidin-2,4-dione or its salts;
5-[4-(4-(2-Amino-2-carboxyethyl)phenoxy)-2-fluorobenzyl]oxazolidin-2,4-dione or its salts;
5-[4-(4-(2-Amino-2-methoxycarbonylethyl)phenoxy)-2-fluorobenzyl]oxazolidin-2,4-dione or its salts;
5-[4-(4-(2-Amino-2-carboxyethyl)phenoxy)-3-fluorobenzilidene]thiazolidin-2,4-dione or its salts;
5-[4-(4-(2-Amino-2-methoxycarbonylethyl)phenoxy)-3-fluorobenzilidene]thiazolidin-2,4-dione or its salts;
5-[4-(4-(2-Amino-2-carboxyethyl)phenoxy)-3-fluorobenzyl]thiazolidin-2,4-dione or its salts;
5-[4-(4-(2-Amino-2-methoxycarbonylethyl)phenoxy)-3-fluorobenzyl]thiazolidin-2,4-dione or its salts;
5-[4-(4-(2-Amino-2-carboxyethyl)phenoxy)-3-fluorobenzilidene]oxazolidin-2,4-dione or its salts;
5-[4-(4-(2-Amino-2-methoxycarbonylethyl)phenoxy)-3-fluorobenzilidene]oxazolidin-2,4-dione or its salts;
5-[4-(4-(2-Amino-2-carboxyethyl)phenoxy)-3-fluorobenzyl]oxazolidin-2,4-dione or its salts;
5-[4-(4-(2-Amino-2-methoxycarbonylethyl)phenoxy)-3-fluorobenzyl]oxazolidin-2,4-dione or its salts;
5-[4-(4-(2-Amino-2-carboxyethyl)phenoxy)-2-trifluoromethylbenzilidene]thiazolidin-2,4-dione or its salts;
5-[4-(4-(2-Amino-2-methoxycarbonylethyl)phenoxy)-2-trifluoromethylbenzilidene]thiazolidin-2,4-dione or its salts;
5-[4-(4-(2-Amino-2-carboxyethyl)phenoxy)-2-trifluoromethylbenzyl]thiazolidin-2,4-dione or its salts;
5-[4-(4-(2-Amino-2-methoxycarbonylethyl)phenoxy)-2-trifluoromethylbenzyl]thiazolidin-2,4-dione or its salts;
5-[4-(4-(2-Amino-2carboxyethyl)phenoxy)-2-trifluoromethylbenzilidene]oxazolidin-2,4-dione or its salts;
5-[4-(4-(2-Amino-2-methoxycarbonylethyl)phenoxy)-2-trifluoromethylbenzilidene]oxazolidin-2,4-dione or its salts;
5-[4-(4-(2-Amino-2-carboxyethyl)phenoxy)-2-trifluoromethylbenzyl]oxazolidin-2,4-dione or its salts;
5-[4-(4-(2-Amino-2-methoxycarbonylethyl)phenoxy)-2-trifluoromethylbenzyl]oxazolidin-2,4-dione or its salts;
5-[4-(4-(2-Amino-2-carboxyethyl)phenoxy)-3-trifluoromethylbenzilidene]thiazolidin-2,4-dione or its salts;
5-[4-(4-(2-Amino-2-methoxycarbonylethyl)phenoxy)-3-trifluoromethylbenzilidene]thiazolidin-2,4-dione or its salts;
5-[4-(4-(2-Amino-2-carboxyethyl)phenoxy)-3-trifluoromethylbenzyl]thiazolidin-2,4-dione or its salts;
5-[4-(4-(2-Amino-2-methoxycarbonylethyl)phenoxy)-3-trifluoromethylbenzyl]thiazolidin-2,4-dione or its salts;
5-[4-(4-(2-Amino-2-carboxyethyl)phenoxy)-3-trifluoromethylbenzilidene]oxazolidin-2,4-dione or its salts;
5-[4-(4-(2-Amino-2-methoxycarbonylethyl)phenoxy)-3-trifluoromethylbenzilidene]oxazolidin-2,4-dione or its salts;
5-[4-(4-(2-Amino-2-carboxyethyl)phenoxy)-3-trifluoromethylbenzyl]oxazolidin-2,4-dione or its salts;
5-[4-(4-(2-Amino-2-methoxycarbonylethyl)phenoxy)-3-trifluoromethylbenzyl]oxazolidin-2,4-dione or its salts;
5-[4-(4-(2-Amino-2-carboxyethyl)-2,6-difluorophenoxy)benzilidene]oxazolidin-2,4-dione or its salts;
5-[4-(4-(2-Amino-2-methoxycarbonylethyl)-2,6-difluorophenoxy)benzilidene]oxazolidin-2,4-dione or its salts
5-[4-(4-(2-Amino-2-carboxyethyl)-2,6-difluorophenoxy)benzyl]oxazolidin-2,4-dione or its salts;
5-[4-(4-(2-Amino-2-methoxycarbonylethyl)-2,6-difluorophenoxy)benzyl]oxazolidin-2,4-dione or its salts;
5-[4-(4-(2-Amino-2-carboxyethyl)-2,6-difluorophenoxy)benzilidene]thiazolidin-2,4-dione or its salts;
5-[4-(4-(2-Amino-2-methoxycarbonylethyl)-2,6-difluorophenoxy)benzilidene]thiazolidin-2,4-dione or its salts;

5-[4-(4-(2-Amino-2-carboxyethyl)-2,6-difluorophenoxy) benzyl]thiazolidin-2,4-dione or its salts;

5-[4-(4-(2-Amino-2-methoxycarbonylethyl)-2,6-difluorophenoxy)benzyl]thiazolidin-2,4-dione or its salts;

5-[4-(4-(2-Amino-2-carboxyethyl)-2,3-difluorophenoxy) benzilidene]thiazolidin-2,4-dione or its salts 5-[4-(4-(2-Amino-2-methoxycarbonylethyl)-2,3-difluorophenoxy)benzilidene]thiazolidin-2,4-dione or its salts;

5-[4-(4-(2-Amino-2-carboxyethyl)-2,3-difluorophenoxy) benzyl]thiazolidin-2,4-dione or its salts;

5-[4-(4-(2-Amino-2-methoxycarbonylethyl)-2,3-difluorophenoxy)benzyl]thiazolidin-2,4-dione or its salts;

5-[4-(4-(2-Amino-2-carboxyethyl)-2,3-difluorophenoxy) benzilidene]oxazolidin-2,4-dione or its salts;

5-[4-(4-(2-Amino-2-methoxycarbonylethyl)-2,3-difluorophenoxy)benzilidene]oxazolidin-2,4-dione or its salts;

5-[4-(4-(2-Amino-2-carboxyethyl)-2,3-difluorophenoxy) benzyl]oxazolidin-2,4-dione or its salts;

5-[4-(4-(2-Amino-2-methoxycarbonylethyl)-2,3-difluorophenoxy)benzyl]oxazolidin-2,4-dione or its salts;

5-[4-(4-(2-Amino-2-carboxyethyl)-3-methylphenoxy) benzilidene]oxazolidin-2,4-dione or its salts;

5-[4-(4-(2-Amino-2-methoxycarbonylethyl)-3-methylphenoxy)benzilidene]oxazolidin-2,4-dione or its salts;

5-[4-(4-(2-Amino-2-carboxyethyl)-3-methylphenoxy) benzyl]oxazolidin-2,4-dione or its salts;

5-[4-(4-(2-Amino-2-methoxycarbonylethyl)-3-methylphenoxy)benzyl]oxazolidin-2,4-dione or its salts;

5-[4-(4-(2-Amino-2-carboxyethyl)-3-methylphenoxy) benzilidene]thiazolidin-2,4-dione or its salts;

5-[4-(4-(2-Amino-2-methoxycarbonylethyl)-3-methylphenoxy)benzilidene]thiazolidin-2,4-dione or its salts;

5-[4-(4-(2-Amino-2-carboxyethyl)-3-methylphenoxy) benzyl]thiazolidin-2,4-dione or its salts;

5-[4-(4-(2-Amino-2-methoxycarbonylethyl)-3-methylphenoxy)benzyl]thiazolidin-2,4-dione or its salts;

5-[4-(4-(2-Amino-2-carboxyethyl)-3-nitrophenoxy) benzilidene]thiazolidin-2,4-dione or its salts;

5-[4-(4-(2-Amino-2-methoxycarbonylethyl)-3-nitrophenoxy)benzilidene]thiazolidin-2,4-dione or its salts;

5-[4-(4-(2-Amino-2-carboxyethyl)-3-nitrophenoxy)benzyl] thiazolidin-2,4-dione or its salts;

5-[4-(4-(2-Amino-2-methoxycarbonylethyl)-3-nitrophenoxy)benzyl]thiazolidin-2,4-dione or its salts;

5-[4-(4-(2-Amino-2-carboxyethyl)-3-nitrophenoxy) benzilidene]oxazolidin-2,4-dione or its salts;

5-[4-(4-(2-Amino-2-methoxycarbonylethyl)-3-nitrophenoxy)benzilidene]oxazolidin-2,4-dione or its salts;

5-[4-(4-(2-Amino-2-carboxyethyl)-3-nitrophenoxy)benzyl] oxazolidin-2,4-dione or its salts;

5-[4-(4-(2-Amino-2-methoxycarbonylethyl)-3-nitrophenoxy)benzyl]oxazolidin-2,4-dione or its salts;

5-[4-(4-(2-Amino-2-carboxyethyl)-3-aminophenoxy) benzilidene]thiazolidin-2,4-dione or its salts;

5-[4-(4-(2-Amino-2-methoxycarbonylethyl)-3-aminophenoxy)benzilidene]thiazolidin-2,4-dione or its salts;

5-[4-(4-(2-Amino-2-carboxyethyl)-3-aminophenoxy) benzyl]thiazolidin-2,4-dione or its salts;

5-[4-(4-(2-Amino-2-methoxycarbonylethyl)-3-aminophenoxy)benzyl]thiazolidin-2,4-dione or its salts;

5-[4-(4-(2-Amino-2-carboxyethyl)-3-aminophenoxy) benzilidene]oxazolidin-2,4-dione or its salts;

5-[4-(4-(2-Amino-2-methoxycarbonylethyl)-3-aminophenoxy)benzilidene]oxazolidin-2,4-dione or its salts;

5-[4-(4-(2-Amino-2-carboxyethyl)-3-aminophenoxy) benzyl]oxazolidin-2,4-dione or its salts;

5-[4-(4-(2-Amino-2-methoxycarbonylethyl)-3-aminophenoxy)benzyl]oxazolidin-2,4-dione or its salts;

5-[4-(4-(2-Amino-2-carboxyethyl)-2-fluorophenoxy) benzilidene]thiazolidin-2,4-dione or its salts;

5-[4-(4-(2-Amino-2-methoxycarbonylethyl)-2-fluorophenoxy)benzilidene]thiazolidin-2,4-dione or its salts;

5-[4-(4-(2-Amino-2-carboxyethyl)-2-fluorophenoxy) benzyl]thiazolidin-2,4-dione or its salts;

5-[4-(4-(2-Amino-2-methoxycarbonylethyl)-2-fluorophenoxy)benzyl]thiazolidin-2,4-dione or its salts;

5-[4-(4-(2-Amino-2-carboxyethyl)-2-fluorophenoxy) benzilidene]oxazolidin-2,4-dione or its salts;

5-[4-(4-(2-Amino-2-methoxycarbonylethyl)-2-fluorophenoxy)benzilidene]oxazolidin-2,4-dione or its salts;

5-[4-(4-(2-Amino-2-carboxyethyl)-2-fluorophenoxy) benzyl]oxazolidin-2,4-dione or its salts;

5-[4-(4-(2-Amino-2-methoxycarbonylethyl)-2-fluorophenoxy)benzyl]oxazolidin-2,4-dione or its salts;

5-[4-(4-(2-Amino-2-carboxyethyl)-3-fluorophenoxy) benzilidene]thiazolidin-2,4-dione or its salts;

5-[4-(4-(2-Amino-2-methoxycarbonylethyl)-3-fluorophenoxy)benzilidene]thiazolidin-2,4-dione or its salts;

5-[4-(4-(2-Amino-2-carboxyethyl)-3-fluorophenoxy) benzyl]thiazolidin-2,4-dione or its salts;

5-[4-(4-(2-Amino-2-methoxycarbonylethyl)-3-fluorophenoxy)benzyl]thiazolidin-2,4-dione or its salts;

5-[4-(4-(2-Amino-2-carboxyethyl)-3-fluorophenoxy) benzilidene]oxazolidin-2,4-dione or its salts;

5-[4-(4-(2-Amino-2-methoxycarbonylethyl)-3-fluorophenoxy)benzilidene]oxazolidin-2,4-dione or its salts;

5-[4-(4-(2-Amino-2-carboxyethyl)-3-fluorophenoxy) benzyl]oxazolidin-2,4-dione or its salts;

5-[4-(4-(2-Amino-2-methoxycarbonylethyl)-3-fluorophenoxy)benzyl]oxazolidin-2,4-dione or its salts;

5-[4-(4-(2-Amino-2-carboxyethyl)-2-trifluoromethylphenoxy)benzilidene]thiazolidin-2,4-dione or its salts;

5-[4-(4-(2-Amino-2-methoxycarbonylethyl)-2-trifluoromethylphenoxy)benzilidene]thiazolidin-2,4-dione or its salts;

5-[4-(4-(2-Amino-2-carboxyethyl)-2-trifluoromethylphenoxy)benzyl]thiazolidin-2,4-dione or its salts;

5-[4-(4-(2-Amino-2-methoxycarbonylethyl)-2-trifluoromethylphenoxy)benzyl]thiazolidin-2,4-dione or its salts;

5-[4-(4-(2-Amino-2-carboxyethyl)-2-trifluoromethylphenoxy)benzilidene]oxazolidin-2,4-dione or its salts;

5-[4-(4-(2-Amino-2-methoxycarbonylethyl)-2-trifluoromethylphenoxy)benzilidene]oxazolidin-2,4-dione or its salts;

5-[4-(4-(2-Amino-2-carboxyethyl)-2-trifluoromethylphenoxy)benzyl]oxazolidin-2,4-dione or its salts;

5-[4-(4-(2-Amino-2-methoxycarbonylethyl)-2-trifluoromethylphenoxy)benzyl]oxazolidin-2,4-dione or its salts;

5-[4-(4-(2-Amino-2-carboxyethyl)-3-trifluoromethylphenoxy)benzilidene]thiazolidin-2,4-dione or its salts;

5-[4-(4-(2-Amino-2-methoxycarbonylethyl)-3-trifluoromethylphenoxy)benzilidene]thiazolidin-2,4-dione or its salts;

5-[4-(4-(2-Amino-2-carboxyethyl)-3-trifluoromethylphenoxy)benzyl]thiazolidin-2,4-dione or its salts;

5-[4-(4-(2-Amino-2-methoxycarbonylethyl)-3-trifluoromethylphenoxy)benzyl]thiazolidin-2,4-dione or its salts;

5-[4-(4-(2-Amino-2-carboxyethyl)-3-trifluoromethylphenoxy)benzilidene]oxazolidin-2,4-dione or its salts;

5-[4-(4-(2-Amino-2-methoxycarbonylethyl)-3-trifluoromethylphenoxy)benzilidene]oxazolidin-2,4-dione or its salts;

5-[4-(4-(2-Amino-2-carboxyethyl)-3-trifluoromethylphenoxy)benzyl]oxazolidin-2,4-dione or its salts;

5-[4-(4-(2-Amino-2-methoxycarbonylethyl)-3-trifluoromethylphenoxy)benzyl]oxazolidin-2,4-dione or its salts;

5-[4-(4-(2-t-butoxycarbonylamino-2-methoxycarbonylethyl)phenoxy)benzilidene]thiazolidin-2,4-dione or its salts;

5-[4-(4-(2-t-butoxycarbonylamino-2-methoxycarbonylethyl)phenoxy)benzyl]thiazolidin-2,4-dione or its salts;

5-[4-(4-(2-t-butoxycarbonylamino-2-methoxycarbonylethyl)phenoxy)benzilidene]oxazolidin-2,4-dione or its salts;

5-[4-(4-(2-t-butoxycarbonylamino-2-methoxycarbonylethyl)phenoxy)benzyl]oxazolidin-2,4-dione or its salts;

5-[4-(4-(2-t-butoxycarbonylamino-2-carboxyethyl)phenoxy)benzilidene]thiazolidin-2,4-dione or its salts;

5-[4-(4-(2-t-butoxycarbonylamino-2-carboxyethyl)phenoxy)benzyl]thiazolidin-2,4-dione or its salts;

5-[4-(4-(2-t-butoxycarbonylamino-2-carboxyethyl)phenoxy)benzilidene]oxazolidin-2,4-dione or its salts and 5-[4-(4-(2-t-butoxycarbonylamino-2-carboxyethyl)phenoxy)benzyl]oxazolidin-2,4-dione or its salts.

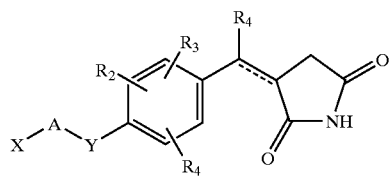

| Compd No. | X | A | Y | $R_2, R_3$ | $R_4$ | Z |
|---|---|---|---|---|---|---|
| 1 | H₂N–CH(COOH)–CH₂– | –C₆H₄– | O | H, H | H | S |
| 2 | H₂N–CH(COOCH₃)–CH₂– | –C₆H₄– | O | H, H | H | S |
| 3 | H₂N–CH(COOH)–CH₂– | –C₆H₄– | O | H, H | 2H | S |
| 4 | H₂N–CH(COOCH₃)–CH₂– | –C₆H₄– | O | H, H | 2H | S |
| 5 | H₂N–CH(COOH)–CH₂– | –C₆H₄– | O | H, H | H | O |
| 6 | H₂N–CH(COOCH₃)–CH₂– | –C₆H₄– | O | H, H | H | O |
| 7 | H₂N–CH(COOH)–CH₂– | –C₆H₄– | O | H, H | 2H | O |

-continued

| Compd No. | X | A | Y | R₂, R₃ | R₄ | Z |
|---|---|---|---|---|---|---|
| 8 | COOCH₃, H₂N, CH₂ | (phenyl) | O | H, H | 2H | O |
| 9 | COOH, H₂N, CH₂ | (phenyl) | O | 2-F, 6-F | H | O |
| 10 | COOCH₃, H₂N, CH₂ | (phenyl) | O | 2-F, 6-F | H | O |
| 11 | COOH, H₂N, CH₂ | (phenyl) | O | 2-F, 6-F | 2H | O |
| 12 | COOCH₃, H₂N, CH₂ | (phenyl) | O | 2-F, 6-F | 2H | O |
| 13 | COOH, H₂N, CH₂ | (phenyl) | O | 2-F, 6-F | H | S |
| 14 | COOCH₃, H₂N, CH₂ | (phenyl) | O | 2-F, 6-F | H | S |
| 15 | COOH, H₂N, CH₂ | (phenyl) | O | 2-F, 6-F | 2H | S |
| 16 | COOCH₃, H₂N, CH₂ | (phenyl) | O | 2-F, 6-F | 2H | S |
| 17 | COOH, H₂N, CH₂ | (phenyl) | O | 2-F, 3-F | H | S |
| 18 | COOCH₃, H₂N, CH₂ | (phenyl) | O | 2-F, 3-F | H | S |
| 19 | COOH, H₂N, CH₂ | (phenyl) | O | 2-F, 3-F | 2H | S |

-continued

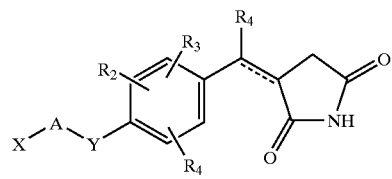

| Compd No. | X | A | Y | R₂, R₃ | R₄ | Z |
|---|---|---|---|---|---|---|
| 20 | COOCH₃, H₂N, CH₂ | (p-phenylene) | O | 2-F, 3-F | 2H | S |
| 21 | COOH, H₂N, CH₂ | (p-phenylene) | O | 2-F, 3-F | H | O |
| 22 | COOCH₃, H₂N, CH₂ | (p-phenylene) | O | 2-F, 3-F | H | O |
| 23 | COOH, H₂N, CH₂ | (p-phenylene) | O | 2-F, 3-F | 2H | O |
| 24 | COOCH₃, H₂N, CH₂ | (p-phenylene) | O | 2-F, 3-F | 2H | O |
| 25 | COOH, H₂N, CH₂ | (p-phenylene) | O | 3-Me | H | O |
| 26 | COOCH₃, H₂N, CH₂ | (p-phenylene) | O | 3-Me | H | O |
| 27 | COOH, H₂N, CH₂ | (p-phenylene) | O | 3-Me | 2H | O |
| 28 | COOCH₃, H₂N, CH₂ | (p-phenylene) | O | 3-Me | 2H | O |
| 29 | COOH, H₂N, CH₂ | (p-phenylene) | O | 3-Me | H | S |
| 30 | COOCH₃, H₂N, CH₂ | (p-phenylene) | O | 3-Me | H | S |
| 31 | COOH, H₂N, CH₂ | (p-phenylene) | O | 3-Me | 2H | S |

-continued

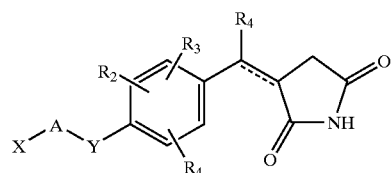

| Compd No. | X | A | Y | R₂, R₃ | R₄ | Z |
|---|---|---|---|---|---|---|
| 32 | COOCH₃, H₂N, CH₂ | (p-phenylene) | O | 3-Me | 2H | S |
| 33 | COOH, H₂N, CH₂ | (p-phenylene) | O | 3-NO₂ | H | S |
| 34 | COOCH₃, H₂N, CH₂ | (p-phenylene) | O | 3-NO₂ | H | S |
| 35 | COOH, H₂N, CH₂ | (p-phenylene) | O | 3-NO₂ | 2H | S |
| 36 | COOCH₃, H₂N, CH₂ | (p-phenylene) | O | 3-NO₂ | 2H | S |
| 37 | COOH, H₂N, CH₂ | (p-phenylene) | O | 3-NO₂ | H | O |
| 38 | COOCH₃, H₂N, CH₂ | (p-phenylene) | O | 3-NO₂ | H | O |
| 39 | COOH, H₂N, CH₂ | (p-phenylene) | O | 3-NO₂ | 2H | O |
| 40 | COOCH₃, H₂N, CH₂ | (p-phenylene) | O | 3-NO₂ | 2H | O |
| 41 | COOH, H₂N, CH₂ | (p-phenylene) | O | 3-NH₂ | H | S |
| 42 | COOCH₃, H₂N, CH₂ | (p-phenylene) | O | 3-NH₂ | H | S |
| 43 | COOH, H₂N, CH₂ | (p-phenylene) | O | 3-NH₂ | 2H | S |

-continued

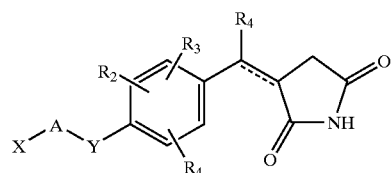

| Compd No. | X | A | Y | R₂, R₃ | R₄ | Z |
|---|---|---|---|---|---|---|
| 44 | COOCH₃, H₂N, CH₂ | (p-phenylene) | O | 3-NH₂ | 2H | S |
| 45 | COOH, H₂N, CH₂ | (p-phenylene) | O | 3-NH₂ | H | O |
| 46 | COOCH₃, H₂N, CH₂ | (p-phenylene) | O | 3-NH₂ | H | O |
| 47 | COOH, H₂N, CH₂ | (p-phenylene) | O | 3-NH₂ | 2H | O |
| 48 | COOCH₃, H₂N, CH₂ | (p-phenylene) | O | 3-NH₂ | 2H | O |
| 49 | COOH, H₂N, CH₂ | (p-phenylene) | O | 2-F | H | S |
| 50 | COOCH₃, H₂N, CH₂ | (p-phenylene) | O | 2-F | H | S |
| 51 | COOH, H₂N, CH₂ | (p-phenylene) | O | 2-F | 2H | S |
| 52 | COOCH₃, H₂N, CH₂ | (p-phenylene) | O | 2-F | 2H | S |
| 53 | COOH, H₂N, CH₂ | (p-phenylene) | O | 2-F | H | O |
| 54 | COOCH₃, H₂N, CH₂ | (p-phenylene) | O | 2-F | H | O |
| 55 | COOH, H₂N, CH₂ | (p-phenylene) | O | 2-F | 2H | O |

-continued

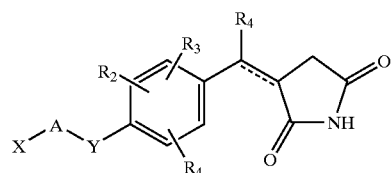

| Compd No. | X | A | Y | R₂, R₃ | R₄ | Z |
|---|---|---|---|---|---|---|
| 56 | COOCH₃, H₂N, CH₂ | (p-phenylene) | O | 2-F | 2H | O |
| 57 | COOH, H₂N, CH₂ | (p-phenylene) | O | 3-F | H | S |
| 58 | COOCH₃, H₂N, CH₂ | (p-phenylene) | O | 3-F | H | S |
| 59 | COOH, H₂N, CH₂ | (p-phenylene) | O | 3-F | 2H | S |
| 60 | COOCH₃, H₂N, CH₂ | (p-phenylene) | O | 3-F | 2H | S |
| 61 | COOH, H₂N, CH₂ | (p-phenylene) | O | 3-F | H | O |
| 62 | COOCH₃, H₂N, CH₂ | (p-phenylene) | O | 3-F | H | O |
| 63 | COOH, H₂N, CH₂ | (p-phenylene) | O | 3-F | 2H | O |
| 64 | COOCH₃, H₂N, CH₂ | (p-phenylene) | O | 3-F | 2H | O |
| 65 | COOH, H₂N, CH₂ | (p-phenylene) | O | 2-CF₃ | H | S |
| 66 | COOCH₃, H₂N, CH₂ | (p-phenylene) | O | 2-CF₃ | H | S |
| 67 | COOH, H₂N, CH₂ | (p-phenylene) | O | 2-CF₃ | 2H | S |

-continued

| Compd No. | X | A | Y | R₂, R₃ | R₄ | Z |
|---|---|---|---|---|---|---|
| 68 | COOCH₃, H₂N, CH₂ | (para-phenylene) | O | 2-CF₃ | 2H | S |
| 69 | COOH, H₂N, CH₂ | (para-phenylene) | O | 2-CF₃ | H | O |
| 70 | COOCH₃, H₂N, CH₂ | (para-phenylene) | O | 2-CF₃ | H | O |
| 71 | COOH, H₂N, CH₂ | (para-phenylene) | O | 2-CF₃ | 2H | O |
| 72 | COOCH₃, H₂N, CH₂ | (para-phenylene) | O | 2-CF₃ | 2H | O |
| 73 | COOH, H₂N, CH₂ | (para-phenylene) | O | 3-CF₃ | H | S |
| 74 | COOCH₃, H₂N, CH₂ | (para-phenylene) | O | 3-CF₃ | H | S |
| 75 | COOH, H₂N, CH₂ | (para-phenylene) | O | 3-CF₃ | 2H | S |
| 76 | COOCH₃, H₂N, CH₂ | (para-phenylene) | O | 3-CF₃ | 2H | S |
| 77 | COOH, H₂N, CH₂ | (para-phenylene) | O | 3-CF₃ | H | O |
| 78 | COOCH₃, H₂N, CH₂ | (para-phenylene) | O | 3-CF₃ | H | O |
| 79 | COOH, H₂N, CH₂ | (para-phenylene) | O | 3-CF₃ | 2H | O |

-continued

| Compd No. | X | A | Y | R₂, R₃ | R₄ | Z |
|---|---|---|---|---|---|---|
| 80 | H₂N-CH(CH₂)-COOCH₃ | 1,4-phenylene | O | 3-CF₃ | 2H | O |
| 81 | H₂N-CH(CH₂)-COOH | 2,3-difluoro-phenylene | O | H, H | H | O |
| 82 | H₂N-CH(CH₂)-COOCH₃ | 2,3-difluoro-phenylene | O | H, H | H | O |
| 83 | H₂N-CH(CH₂)-COOH | 2,3-difluoro-phenylene | O | H, H | 2H | O |
| 84 | H₂N-CH(CH₂)-COOCH₃ | 2,3-difluoro-phenylene | O | H, H | 2H | O |
| 85 | H₂N-CH(CH₂)-COOH | 2,3-difluoro-phenylene | O | H, H | H | S |
| 86 | H₂N-CH(CH₂)-COOCH₃ | 2,3-difluoro-phenylene | O | H, H | H | S |
| 87 | H₂N-CH(CH₂)-COOH | 2,3-difluoro-phenylene | O | H, H | 2H | S |

-continued

| Compd No. | X | A | Y | R₂, R₃ | R₄ | Z |
|---|---|---|---|---|---|---|
| 88 | COOCH₃, H₂N-CH-CH₂ | 2,3-F,F-phenyl (2,5 attachment) | O | H, H | 2H | S |
| 89 | COOH, H₂N-CH-CH₂ | 2,3-F,F-phenyl | O | H, H | H | S |
| 90 | COOCH₃, H₂N-CH-CH₂ | 2,3-F,F-phenyl | O | H, H | H | S |
| 91 | COOH, H₂N-CH-CH₂ | 2,3-F,F-phenyl | O | H, H | 2H | S |
| 92 | COOCH₃, H₂N-CH-CH₂ | 2,3-F,F-phenyl | O | H, H | 2H | S |
| 93 | COOH, H₂N-CH-CH₂ | 2,3-F,F-phenyl | O | H, H | H | O |
| 94 | COOCH₃, H₂N-CH-CH₂ | 2,3-F,F-phenyl | O | H, H | H | O |
| 95 | COOH, H₂N-CH-CH₂ | 2,3-F,F-phenyl | O | H, H | 2H | O |

-continued
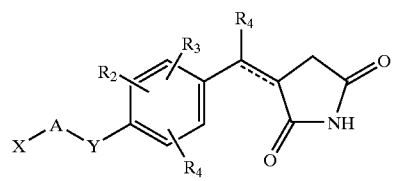
| Compd No. | X | A | Y | R₂, R₃ | R₄ | Z |
|---|---|---|---|---|---|---|
| 96 | COOCH₃, H₂N-CH₂ | 2,3-difluorophenyl | O | H, H | 2H | O |
| 97 | COOH, H₂N-CH₂ | 3-fluorophenyl | O | H, H | H | O |
| 98 | COOCH₃, H₂N-CH₂ | 3-fluorophenyl | O | H, H | H | O |
| 99 | COOH, H₂N-CH₂ | 3-fluorophenyl | O | H, H | 2H | O |
| 100 | COOCH₃, H₂N-CH₂ | 3-fluorophenyl | O | H, H | 2H | O |
| 101 | COOH, H₂N-CH₂ | 3-fluorophenyl | O | H, H | H | S |
| 102 | COOCH₃, H₂N-CH₂ | 3-fluorophenyl | O | H, H | H | S |
| 103 | COOH, H₂N-CH₂ | 3-fluorophenyl | O | H, H | 2H | S |

-continued
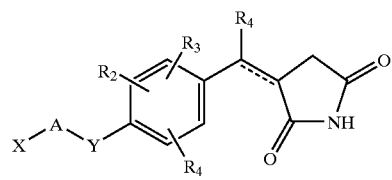
| Compd No. | X | A | Y | R₂, R₃ | R₄ | Z |
|---|---|---|---|---|---|---|
| 104 | COOCH₃, H₂N-CH₂ | (2-F, 4-methyl phenyl) | O | H, H | 2H | S |
| 105 | COOH, H₂N-CH₂ | (3-CH₃, 4-methyl phenyl) | O | H, H | H | O |
| 106 | COOCH₃, H₂N-CH₂ | (3-CH₃, 4-methyl phenyl) | O | H, H | H | O |
| 107 | COOH, H₂N-CH₂ | (3-CH₃, 4-methyl phenyl) | O | H, H | 2H | O |
| 108 | COOCH₃, H₂N-CH₂ | (3-CH₃, 4-methyl phenyl) | O | H, H | 2H | O |
| 109 | COOH, H₂N-CH₂ | (3-CH₃, 4-methyl phenyl) | O | H, H | H | S |
| 110 | COOCH₃, H₂N-CH₂ | (3-CH₃, 4-methyl phenyl) | O | H, H | H | S |
| 111 | COOH, H₂N-CH₂ | (3-CH₃, 4-methyl phenyl) | O | H, H | 2H | S |

-continued
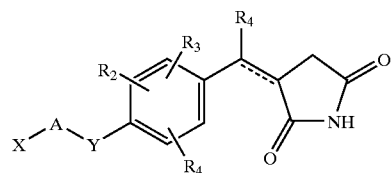
| Compd No. | X | A | Y | R₂, R₃ | R₄ | Z |
|---|---|---|---|---|---|---|
| 112 | 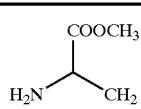 | 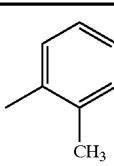 | O | H, H | 2H | S |
| 113 | 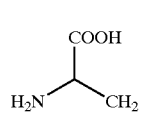 | 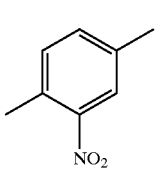 | O | H, H | H | S |
| 114 | 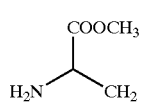 | 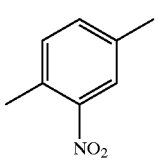 | O | H, H | H | S |
| 115 | 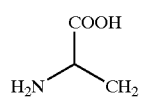 | 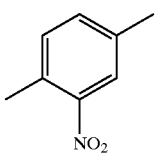 | O | H, H | 2H | S |
| 116 | 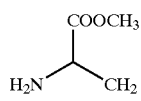 | 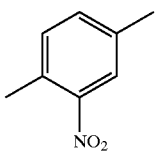 | O | H, H | 2H | S |
| 117 | 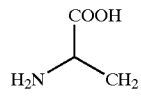 | 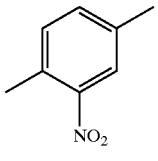 | O | H, H | H | O |
| 118 | 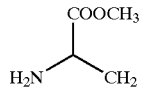 | 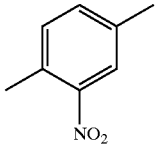 | O | H, H | H | O |
| 119 | 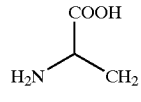 | 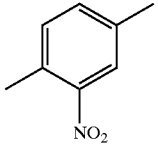 | O | H, H | 2H | O |

-continued
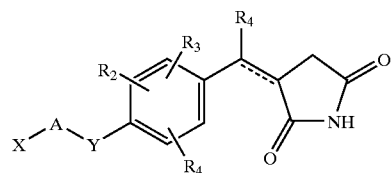
| Compd No. | X | A | Y | R$_2$, R$_3$ | R$_4$ | Z |
|---|---|---|---|---|---|---|
| 120 | COOCH$_3$, H$_2$N-CH-CH$_2$ | 2-methyl-5-yl-4-NO$_2$ | O | H, H | 2H | O |
| 121 | COOH, H$_2$N-CH-CH$_2$ | 2-methyl-5-yl-4-NH$_2$ | O | H, H | H | S |
| 122 | COOCH$_3$, H$_2$N-CH-CH$_2$ | 2-methyl-5-yl-4-NH$_2$ | O | H, H | H | S |
| 123 | COOH, H$_2$N-CH-CH$_2$ | 2-methyl-5-yl-4-NH$_2$ | O | H, H | 2H | S |
| 124 | COOCH$_3$, H$_2$N-CH-CH$_2$ | 2-methyl-5-yl-4-NH$_2$ | O | H, H | 2H | S |
| 125 | COOH, H$_2$N-CH-CH$_2$ | 2-methyl-5-yl-4-NH$_2$ | O | H, H | H | O |
| 126 | COOCH$_3$, H$_2$N-CH-CH$_2$ | 2-methyl-5-yl-4-NH$_2$ | O | H, H | H | O |
| 127 | COOH, H$_2$N-CH-CH$_2$ | 2-methyl-5-yl-4-NH$_2$ | O | H, H | 2H | O |

-continued

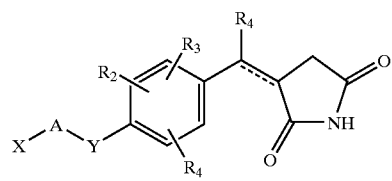

| Compd No. | X | A | Y | R$_2$, R$_3$ | R$_4$ | Z |
|---|---|---|---|---|---|---|
| 128 | H$_2$N-CH(COOCH$_3$)-CH$_2$- | 2,4-disubst. phenyl with NH$_2$ | O | H, H | 2H | O |
| 129 | H$_2$N-CH(COOH)-CH$_2$- | 2,4-disubst. phenyl with F | O | H, H | H | S |
| 130 | H$_2$N-CH(COOCH$_3$)-CH$_2$- | 2,4-disubst. phenyl with F | O | H, H | H | S |
| 131 | H$_2$N-CH(COOH)-CH$_2$- | 2,4-disubst. phenyl with F | O | H, H | 2H | S |
| 132 | H$_2$N-CH(COOCH$_3$)-CH$_2$- | 2,4-disubst. phenyl with F | O | H, H | 2H | S |
| 133 | H$_2$N-CH(COOH)-CH$_2$- | 2,4-disubst. phenyl with F | O | H, H | H | O |
| 134 | H$_2$N-CH(COOCH$_3$)-CH$_2$- | 2,4-disubst. phenyl with F | O | H, H | H | O |
| 135 | H$_2$N-CH(COOH)-CH$_2$- | 2,4-disubst. phenyl with F | O | H, H | 2H | O |
| 136 | H$_2$N-CH(COOCH$_3$)-CH$_2$- | 2,4-disubst. phenyl with F | O | H, H | 2H | O |
| 137 | H$_2$N-CH(COOH)-CH$_2$- | 2,4-disubst. phenyl with F | O | H, H | H | S |

-continued

| Compd No. | X | A | Y | R₂, R₃ | R₄ | Z |
|---|---|---|---|---|---|---|
| 138 | H₂N-CH(COOCH₃)-CH₂- | 3-F-phenyl | O | H, H | H | S |
| 139 | H₂N-CH(COOH)-CH₂- | 3-F-phenyl | O | H, H | 2H | S |
| 140 | H₂N-CH(COOCH₃)-CH₂- | 3-F-phenyl | O | H, H | 2H | S |
| 141 | H₂N-CH(COOH)-CH₂- | 3-F-phenyl | O | H, H | H | O |
| 142 | H₂N-CH(COOCH₃)-CH₂- | 3-F-phenyl | O | H, H | H | O |
| 143 | H₂N-CH(COOH)-CH₂- | 3-F-phenyl | O | H, H | 2H | O |
| 144 | H₂N-CH(COOCH₃)-CH₂- | 3-F-phenyl | O | H, H | 2H | O |
| 145 | H₂N-CH(COOH)-CH₂- | 2-CF₃-phenyl | O | H, H | H | S |
| 146 | H₂N-CH(COOCH₃)-CH₂- | 2-CF₃-phenyl | O | H, H | H | S |

-continued
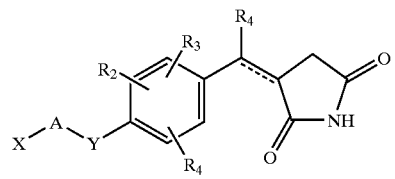
| Compd No. | X | A | Y | R₂, R₃ | R₄ | Z |
|---|---|---|---|---|---|---|
| 147 | HOOC-CH(NH₂)-CH₂- | 2,4-disub-phenyl-CF₃ | O | H, H | 2H | S |
| 148 | CH₃OOC-CH(NH₂)-CH₂- | 2,4-disub-phenyl-CF₃ | O | H, H | 2H | S |
| 149 | HOOC-CH(NH₂)-CH₂- | 2,4-disub-phenyl-CF₃ | O | H, H | H | O |
| 150 | CH₃OOC-CH(NH₂)-CH₂- | 2,4-disub-phenyl-CF₃ | O | H, H | H | O |
| 151 | HOOC-CH(NH₂)-CH₂- | 2,4-disub-phenyl-CF₃ | O | H, H | 2H | O |
| 152 | CH₃OOC-CH(NH₂)-CH₂- | 2,4-disub-phenyl-CF₃ | O | H, H | 2H | O |
| 153 | HOOC-CH(NH₂)-CH₂- | phenyl-CF₃ | O | H, H | H | S |
| 154 | CH₃OOC-CH(NH₂)-CH₂- | phenyl-CF₃ | O | H, H | H | S |
| 155 | HOOC-CH(NH₂)-CH₂- | phenyl-CF₃ | O | H, H | 2H | S |

-continued

| Compd No. | X | A | Y | R₂, R₃ | R₄ | Z |
|---|---|---|---|---|---|---|
| 156 | H₂N-CH(COOCH₃)-CH₂- | 4-CF₃-phenyl | O | H, H | 2H | S |
| 157 | H₂N-CH(COOH)-CH₂- | 4-CF₃-phenyl | O | H, H | H | O |
| 158 | H₂N-CH(COOCH₃)-CH₂- | 4-CF₃-phenyl | O | H, H | H | O |
| 159 | H₂N-CH(COOH)-CH₂- | 4-CF₃-phenyl | O | H, H | 2H | O |
| 160 | H₂N-CH(COOH)-CH₂- | 4-CF₃-phenyl | O | H, H | 2H | O |
| 161 | (CH₃)₃C-O-C(O)-NH-CH(COOCH₃)-CH₂- | phenyl | O | H, H | H | S |
| 162 | (CH₃)₃C-O-C(O)-NH-CH(COOCH₃)-CH₂- | phenyl | O | H, H | 2H | S |
| 163 | (CH₃)₃C-O-C(O)-NH-CH(COOCH₃)-CH₂- | phenyl | O | H, H | H | O |

-continued

| Compd No. | X | A | Y | $R_2, R_3$ | $R_4$ | Z |
|---|---|---|---|---|---|---|
| 164 | H3C—C(CH3)2—O—C(O)—NH—CH(CH2)—COOCH3 | (p-phenylene) | O | H, H | 2H | O |
| 165 | H3C—C(CH3)2—O—C(O)—NH—CH(CH2)—COOH | (p-phenylene) | O | H, H | H | S |
| 166 | H3C—C(CH3)2—O—C(O)—NH—CH(CH2)—COOH | (p-phenylene) | O | H, H | 2H | S |
| 167 | H3C—C(CH3)2—O—C(O)—NH—CH(CH2)—COOH | (p-phenylene) | O | H, H | H | O |
| 168 | H3C—C(CH3)2—O—C(O)—NH—CH(CH2)—COOH | (p-phenylene) | O | H, H | 2H | O |

Preferred salts for the list of compounds above are hydrochloride, hydrobromide, sodium, potassium or magnesium.

According to another feature of the present invention, there is provided a process for the preparation of compounds of formula (I), wherein - - - represents a bond and all other symbols are as defined earlier, as shown in scheme-I Scheme-I

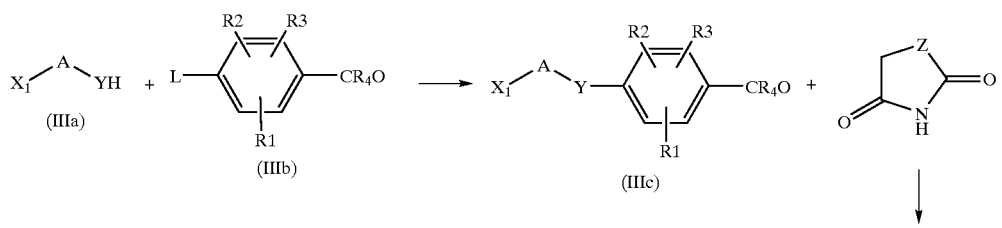

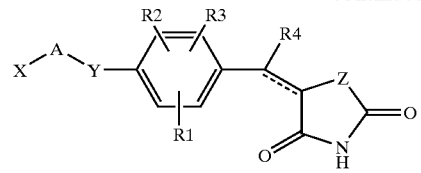 (I)

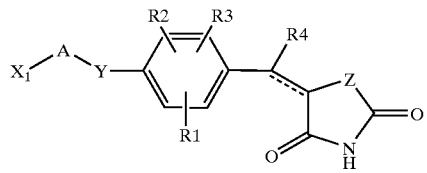 (IIId)

The reaction of compound of formula (IIIa) wherein $X_1$ represents a protected alpha amino carboxylic acid group and all other symbols are as defined earlier with the compound of formula (IIIb) wherein L represents a nucleophilic aromatic substitution leaving group, and all other symbols are as defined earlier to produce a compound of formula (IIIc) may be carried out in the presence of solvents such as THF, DMF, DMSO, DME and the like or mixtures of solvents may be used. The reaction may be carried out in an inert atmosphere which may be maintained by using inert gases such as $N_2$, Ar or He. The reaction may be effected in the presence of a base such as $K_2CO_3$, $Na_2CO_3$, NaH or mixtures thereof. The reaction temperature may range from 20° C. to 150° C., preferably at a temperature in the range of 30° C. to 100° C. The duration of the reaction may range from 1 to 24 hours, preferably from 2 to 6 hours.

The conventional protecting groups used are those that can be easily removed and are selected from t-Boc, CBz, F-moc, etc.

The reaction of the compound of the general formula (IIIc) with 2,4-thiazolidinedione or 2,4-oxazolidinedione to yield a compound of formula (IIId) may be carried out neat in the presence of sodium acetate or in the presence of a solvent such as benzene, toluene, methoxyethanol or mixtures thereof. The reaction temperature may range from 80° C. to 180° C., when the reaction is carried out neat in the presence of sodium acetate. Suitable catalyst such as piperidinium acetate or benzoate, sodium acetate or mixtures of catalysts may also be employed. Sodium acetate can be used in the presence of solvent, but it is preferred that sodium acetate is used neat. The water produced in the reaction may be removed, for example, by using Dean Stark water separator or by using water absorbing agents like molecular sieves.

The deprotection of amino acid group of formula (IIId) to yield compound of formula (I) may be carried out using acids such as HCl, sulfuric acid, acetic acid in the presence of solvents such as DCM, ethyl acetate, water and the like or mixture thereof at a temperature in the range of −10° C. to 50° C.

In another embodiment of the present invention, the compounds of general formula (I) wherein Z represents sulfur, - - - represents no bond can be prepared by reacting the compound of formula (IIIe)

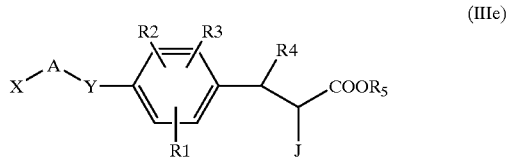 (IIIe)

wherein J is halogen atom, like chlorine, bromine or iodine and $R_5$ is a lower alkyl group with thiourea followed by treatment with an acid.

The reaction of compound of general formula (IIIe) with thiourea is carried out in the presence of alcoholic solvent such as methanol, ethanol, propanol, isobutanol, 2-methoxybutanol, etc or DMSO or sulfolane. The reaction may be conducted at a temperature in the range between 20° C. and the reflux temperature of the solvent used. Bases such as NaOAc, KOAc, NaOMe, NaOEt etc. can be used.

In yet another embodiment of the present invention, the compounds of the general formula (I) wherein - - - represents a bond and all other symbols are as defined earlier can also be prepared by reacting a compound of formula (IIIf)

 (IIIf)

wherein L is a nucleophilic leaving such as halogen atom, like chlorine, bromine or iodine; methanesulfonate, trifluoromethanesulfonate, p-toluenesulfonate and the like with a compound of the formula (IIIg).

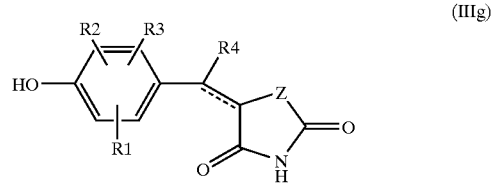 (IIIg)

The reaction of compound of general formula (IIIf) with a compound of general formula (IIIg) to produce a compound of general formula (I) may be carried out in the presence of solvents such as THF, DMF, DMSO, DME and the like or mixtures thereof. The reaction may be carried out in an inert atmosphere which may be maintained by using inert gases such as $N_2$, Ar or He. The reaction may be effected in the presence of a base such as alkalis like sodium hydroxide or potassium hydroxide; alkali metal carbonates like sodium carbonate or potassium carbonate; alkali metal hydrides such as sodium hydride; organometallic bases like n-butyl lithium; alkali metal amides like sodamide, or mixtures thereof. Multiple solvents and bases can be used. The amount of base may range from 1 to 5 equivalents, preferably 1 to 3 equivalents. The reaction temperature may be in the range of 0° C. to 120° C., preferably at a temperature in the range of 20° C. to 100° C. The duration of the reaction may range from 0.5 to 24 hours, preferably from 0.5 to 6 hrs.

In yet another embodiment of the present invention, the compounds of the general formula (I) wherein - - - represents a bond and all other symbols are as defined earlier can also be prepared by reacting a compound of formula (IIIh)

(IIIh)

where A and X are as defined earlier with a compound of the formula (IIIg).

(IIIg)

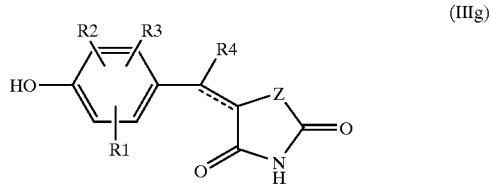

The reaction of compound of general formula (IIIh) with a compound of general formula (IIIg) to produce a compound of general formula (I) may be carried out in the presence of solvents such as THF, DMF, DMSO, DME and the like or mixtures thereof. The reaction may be carried out in an inert atmosphere which may be maintained by using inert gases such as $N_2$, Ar or He. The reaction may be effected in the presence of a base such as alkalis like sodium hydroxide or potassium hydroxide; alkali metal carbonates like sodium carbonate or potassium carbonate; alkali metal hydrides such as sodium hydride; organometallic bases like n-butyl lithium; alkali metal hydrides like sodamide, or mixtures thereof. Multiple solvents and bases can be used. The amount of base may range from 1 to 5 equivalents, preferably 1 to 3 equivalents. The reaction temperature may be in the range of 0° C. to 120° C., preferably at a temperature in the range of 20° C. to 100° C. The duration of the reaction may range from 0.5 to 24 hours, preferably from 0.5 to 6 hrs.

In another embodiment of the present invention, there is provided a process for the preparation of compounds of formula (I), wherein - - - represents no bond by reducing compounds of formula (I) wherein - - - represents a bond and all other symbols are as defined earlier. The reduction may be carried out in the presence of gaseous hydrogen and a catalyst such as Pd/C, Rh/C, Pt/C, Raney Nickel, and the like. Mixtures of catalysts may be used. The reaction may be conducted in the presence of solvents such as dioxane, acetic acid, ethyl acetate and the like. Mixtures of solvents may be used. A pressure between atmospheric pressure to 100 psi may be employed. The catalyst may be 5–10% Pd/C and the amount of catalyst used may range from 50–300% w/w. The reaction may also be carried out by employing metal solvent reduction such as magnesium in methanol or sodium amalgam in methanol. The reaction may also be carried out with alkali metal borohydrides such as $LiBH_4$, $NaBH_4$, $KBH_4$ and the like in the presence of cobalt salt such as $CoCl_2$ and ligands, preferably bidentated ligands such as 2,2'-bipyridyl, 1,10-phenanthroline, bisoximes and the like.

In yet another embodiment of the present invention, there is provided an intermediate of formula (IIIc)

(IIIc)

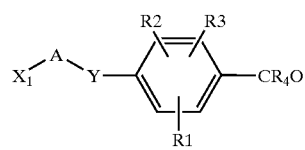

their derivatives, their analogs, their tautomeric forms, their stereoisomers, their polymorphs, their pharmaceutically acceptable salts, their pharmaceutically acceptable solvates, wherein Y represents oxygen, sulfur or NR, wherein R represents hydrogen or alkyl; $R_1$, $R_2$, $R_3$ and $R_4$ may be same or different and independently represent hydrogen, halogen, hydroxy, nitro, cyano, formyl, amino, alkyl, or alkoxy; A represents substituted or unsubstituted aryl; X represents an alpha amino carboxylic acid or its derivatives bonded to A through its alpha side chain.

In yet another embodiment of the present invention, there is provided an intermediate of formula (IIIe)

(IIIe)

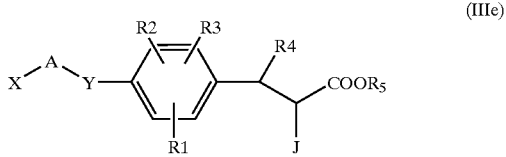

their derivatives, their analogs, their tautomeric forms, their stereoisomers, their polymorphs, their pharmaceutically acceptable salts, their pharmaceutically acceptable solvates, wherein Y represents oxygen, sulfur or NR, wherein R represents hydrogen or alkyl; $R_1$, $R_2$, $R_3$ and $R_4$ may be same or different and independently represent hydrogen, halogen, hydroxy, nitro, cyano, formyl, amino, alkyl, or alkoxy; A represents substituted or unsubstituted aryl; X represents an alpha amino carboxylic acid or its derivatives bonded to A through its alpha side chain; J represents halogen atom and $R_5$ represents lower alkyl group.

It has been surprisingly found that, unlike other thiazolidine-compounds (TZD molecules), compounds of the invention exhibit no adipocyte differentiation. It is also surprising that administration reduces body weight gain. Finally, compounds of the invention appear to have no affinity for PPAR-g. These three features of the compounds are different from known TZD molecules, which typically have adipocyte differentiation activity, increase weight gain, and are PPAR-g agonists. Furthermore, compounds of the invention have anti-inflammation properties. For example, the compounds inhibit TNFα, IL-6 and IL-1β.

The compounds according to the present invention may be combined with a physiologically acceptable vehicle in a pharmaceutical composition. The particularly preferred form of composition is an orally administrated capsule or solution in which the compound is delivered in water, saline, a phosphate buffer, or lyophilized powder in a form of tablets or capsules which also includes various fillers and binders. The effective dosages of compound in a composition will be selected by those of ordinary skill in the art and may be empirically determined.

The compounds of the present invention are useful for the treatment of inflammation, autoimmune diseases such as multiple sclerosis, IBD, obesity, neurological diseases, hypertension, and diseases such as diabetes characterized by the presence of elevated blood glucose levels, that is hyperglycemic disorders such as diabetes mellitus, including both Type I and Type II diabetes as well as other hyperglycemic related disorders such as hyperlipidemia, kidney related disorders, and the like.

By "treatment," it is meant that the compound is administered at least to reduce inflammation, hypertension, obesity, blood lipid levels, blood glucose levels or symptoms associated with autoimmune or neurological disease or disorder from which the patient is suffering. The compound is administered in an amount sufficient, for example, to reduce blood glucose level to an acceptable range, wherein an acceptable range means +/−10%, usually +/−8% and usually +/−5% of the normal average blood glucose level for the subject. A variety of subjects may be treated with the compounds such as livestock, valuable or rare animals, pets, as well as humans. The compounds may be administered to the subject using a convenient administration technique, including intravenous, intradermal, intramuscular, subcutaneous, oral administration and the like. However, the oral route of administration is particularly preferred. The dosage delivered to the host will necessarily depend upon the route by which the compound is delivered, but generally ranges from 5 to 500 mg/70 kg human body weight.

The invention is explained in detail in the examples given below which are provided by way of illustration only and therefore should not be construed to limit the scope of the invention.

EXAMPLE 1

Preparation of 5-[4-(4-(2-amino-2-methoxycarbonylethyl)phenoxy)benzyl]thiazolidin-2,4-dione hydrochloride salt

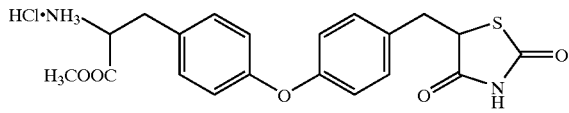

Step (i)

Preparation of methyl-2-[(t-butoxycarbonyl)amino]-3-[-(4-formylphenoxy)phenyl]propanoate To a suspension of fresh sodium hydride (0.813 g, 33.9 mmol) in dry DMF (20 ml) under nitrogen atmosphere was added the solution of methyl-2-[(t-butoxycarbonyl)amino]-3-(4-hydroxyphenyl)propanoate (10 g, 33.9 mmol) in DMF (20 ml) slowly. The mixture was stirred for 15 minutes. 4-Fluorobenzaldehyde (4.20 g, 33.9 mmol) was added and the mixture was heated to 80° C. After completion of the reaction, the solvent was removed by high vacuum and the mixture was quenched with addition of saturated aqueous ammonium chloride. The mixture was extracted with ethyl acetate (3×50 ml). After washing with brine and dried on anhydrous sodium sulfate, the solvent was evaporated and the product was purified with flash column from eluent of hexanes: ethyl ether; 12/30 to 12/22 to afford the title compound as an oil (yield 11.5 g, 85.0%).

$^1$H NMR (CDCl$_3$, 360 MHz,): δ 9.92 (s, 1H), 7.83 (d, 2H), 7.19 (d, 2H), 7.05 (d, 2H), 7.03 (d, 2H), 4.60 (t, 1H), 3.72 (s, 3H), 3.09 (d, 2H), 1.42(s, 9H). The structure was confirmed by Spec. Calculated (M+1) 400.4; Measured 400.3.

Step (ii)

Preparation of 5-[4-(4-(2-t-butoxycarbonylamino-2-methoxycarbonylethyl)phenoxy)benzilidene]thiazolidin-2,4-dione To a solution of methyl-2-[(t-butoxycarbonyl)amino]-3-[-(4-formylphenoxy)phenyl]propanoate obtained in step (i) above in anhydrous toluene (10 g, 25 mmol), 2,4-thiazolidinedione (3.53 g, 30 mmol) was added followed by benzoic acid (0.46 g, 3.75 mmol) and piperidine (0.28 g, 3.25 mmol). The solution was heated to reflux at 145–155° C. with continuous removal of water using Dean-Stark apparatus for 5 hr. The solution was cooled to RT and the yellow solid was precipitated to afford the title compound (yield 11.9 g, 96%, purity 96.5% by HPLC, mp: 160–164° C.).

$^1$H NMR (CDCl$_3$, 360 MHz,): 7.82 (s, 1H), 7.47 (d, 2H); 7.05 (d, 2H), 7.00 (d, 2H); 6.75 (d, 2H) 5.18 (m, 1H), 4.54 (M, 1H), 3.71 (s, 3H); 3.02 (m, 2H), 3.00 (m, 2H). 1.42 (s, 9H). The structure was confirmed by Mass Spec. Calculated (M+1) 498.5; Measured 498.5.

Step (iii)

Preparation 5-[4-(4-(2-amino-2-methoxycarbonylethyl)phenoxy)benzilidene]thiazolidin-2,4-dione A solution of 5-[4-(4-(2-t-butoxycarbonylamino-2-methoxycarbonylethyl)phenoxy)benzilidene]thiazolidin-2,4-dione (2 g, 4.0 mmol) in DCM (100 ml) at 0° C. was bubbled with HCl gas. After stirring for 1 hour, the yellow precipitate was filtered and 1.7 g (3.9 mmol) of HCl-Tyr (C6H4-CH=TDZ)-OMe was collected with 97.5% yield, mp: 187–190° C. The HPLC purity of product was 94.5%. Compound 1.

$^{1H}$ NMR (D2O, 360 MHz,): 7.46 (s, NH, 1H); 7.24 (d, 2H); 7.16 (d, 2H); 6.94 (d, 2H); 6.78 (d, 2H); 4.80 (s, NH3, 3H); 4.40 (m, Cα-H, 1H); 3.80 (s, OMe). The structure was confirmed by Mass Spec. Calculated (M+1) 501.5; Measured 501.5.

Step (iv)

Preparation of 5-[4-(4-(2-amino-2-methoxycarbonylethyl)phenoxy)benzyl]thiazolidin-2,4-dione To a solution of 5-[4-(4-(2-amino-2-methoxycarbonylethyl)phenoxy)benzilidene]thiazolidin-2,4-dione (0.7 g, 1.6 mmol) in methanol (20 ml) dry Pd/C (0.15 g) was added. After hydrogenating at 60 psi at 40° C. over night, the solution was filtered with Celite and evaporated under reduced pressure to yield quantitatively the title compound. This compound did not show melting in DSC but changes to black colour, in capillary and shrinks at 97–133° C. Compound 2.

The pharmaceutically acceptable salts may be prepared by reacting the compound of formula (I) with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol etc. Mixtures of solvents may be used. Organic bases like lysine, arginine, diethanolamine, choline, guanidine and their derivatives etc. may also be used. Alternatively, acid addition salts are prepared by treatment with acids such as hydrochloric acid, hydrobromic acid, nitric acid, sulfuric acid, phosphoric acid, p-toluenesulfonic acid, methanesulfonic acid, acetic acid, citric acid, maleic acid, salicylic acid, hydroxynaphthoic acid, ascorbic acid, palmitic acid, succinic acid, benzoic acid, benzene sulfonic acid, tartaric acid and the like in solvents like ethyl acetate, ether, alcohols, acetone, THF, dioxane etc. Mixture of solvents may also be used.

The present invention also provides a pharmaceutical composition, containing one or more of the compounds of the general formula (I) as defined above, their tautomeric forms, their derivatives, their analogues, their stereoisomers, their polymorphs, their pharmaceutically acceptable salts, their pharmaceutically acceptable solvates in combination with the usual pharmaceutically employed carriers, diluents and the like.

The pharmaceutical composition may be in the forms normally employed, such as tablets, capsules, powders, syrups, solutions, suspensions and the like, may contain flavourants, sweeteners etc. in suitable solid or liquid carriers or diluents, or in suitable sterile media to form injectable solutions or suspensions. Such compositions typically contain from 1 to 25%, preferably 1 to 15% by weight of active compound, the remainder of the composition being pharmaceutically acceptable carriers, diluents, excipients or solvents.

Suitable pharmaceutically acceptable carriers include solid fillers or diluents and sterile aqueous or organic solutions. The active compound will be present in such pharmaceutical compositions in the amounts sufficient to provide the desired dosage in the range as described above. Thus, for oral administration, the compounds can be combined with a suitable solid or liquid carrier or diluent to form capsules, tablets, powders, syrups, solutions, suspensions and the like. The pharmaceutical compositions, may, if desired, contain additional components such as flavourants, sweeteners, excipients and the like. For parenteral administration, the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or alkali or alkaline earth metal salts of the compounds. The injectable solutions prepared in this manner can then be, administered intravenously, intraperitoneally, subcutaneously, or intramuscularly, with intramuscular administration being preferred in humans.

The pharmaceutical composition of the present invention are particularly effective in lowering blood glucose, serum insulin and triglyceride levels in animal models of types II diabetes. The pharmaceutical compositions of the present invention are also effective in the treatment of obesity, inflammation, autoimmune diseases. Furthermore, pharmaceutical composition of the present invention are useful for the treatment of disorders associated with insulin resistance, such as polycystic ovary syndrome, as well as hyperlipidemia, coronary artery disease and peripheral vascular disease, and for the treatment of inflammation and immunological diseases, particularly those mediated by cytokines such as TNF-$\alpha$, IL-1, IL-6 and cyclooxygenase such as COX-2.

Protocols for Biological Testing

Compounds of the present invention have been tested for lowering inflammatory cytokines level, chemically-induced inflammation, obesity and blood glucose, in different models for their biological activity. The attached FIGS. 1–9 shows the activity profile of the representative compound.

FIG. 1. Compounds 1 and 2 in Example 1 Inhibit Major Pro-inflammatory Cytokines in Human Monocyte Cells Human THP-1 monocyte cells were cultured and incubated with two compounds of example 1 at different concentrations. Cells were then challenged with lipopolysaccharides (LPS) at a concentration of (1 microgram/ml) for 24 hours. Cell supernatants were then analyzed for the presence of TNF$\alpha$, IL1$\beta$ and IL-6 cytokines by antibody directed enzyme-linked immunoassay. As shown in FIG. 1, the example compounds can inhibit the production of three major pro-infalmmatory cytokines in a dose dependent manner. No significant change in cell viability was observed with incubation of cells in the presence of highest concentration of the compound. These strongly indicate that compound of example 1 is highly effective in reducing the production of pro-inflammatory cytokines.

FIG. 2. Compound 2 in Example 1 can Lower Carrageenan Induced Inflammation in Rats.

Spegue-Dowley rats of average weight 250 g (6–7 weeks of age) were randomized in three goups, and given 50 mg/kg oral dose of compound of example 1. Thirty minutes later carrageenan was administered in the sub-planter region of right hind paws. Control group received equal volume of water without any compound. Paw volume was measured after 2 and three hours. Dexamethasone at a concentration of 5 mg/kg was used as a positive control in this experiment. As shown in FIG. 2, the compound of example 1 can substantially lower the inflammation induced by carrageenan. At time 3 hours the effect of compound of example-1 was as effective as dexamethasone (a known anti-inflammatory drug that acts via different mechanism pathways).

FIG. 3. Compounds 1 and 2 in Example 1 Prevent EAE in Mice (Multiple Sclerosis Model)

Multiple sclerosis (MS) is an autoimmune disease and is regulated by cytokine levels. In order to test the effect of example 1 in MS model, experimental allergic encepahalomyalitis (EAE) was induced in SJL/J mice. EAE is an autoimmune inflammatory disease of the central nervous system (CNS). The disease shows many similarities with the human MS, and hence is used as a model to test the potential efficacy of new drugs that may have applicability in MS. EAE was induced by injecting spinal chord homogenate where animals were treated with example compounds. The severity of EAE was established by clinical scores of paralysis. As shown in FIG. 3, the new compound treated group showed complete prevention of EAE. These results indicate utility of the example compounds for the treatment of MS and other neurological disorders.

FIG. 4. Schematic Representation of Cytokine Modulation and Immune Disorders.

Macrophage produces various cytokines upon stimulation by mitogens and other unknown factors. Few of theses key cytokines are known to be involved in various immunological disorders including a number of autoimmne diseases.

FIG. 5. Direct and Indirect Linkage of TNF$\alpha$ in Metabolic Diseases.

It has been well established that TNF$\alpha$ plays a major role in inflammatory diseases and autoimmune disorders with treatments available for rheumatoid arthritis using antibody against TNF$\alpha$. In addition, a number of studies in recent years have predicted the possible role of TNF$\alpha$ in adipose biology and metabolic disorders such as diabetes, obesity, hyperlipidemic and vascular complications. The schematic illustration reflects how the regulation of TNF$\alpha$ can have impact on a number of metabolic diseases, that can provide different pathways for treating these diseases.

FIG. 6. Compound 2 in Example 1 Substantially Improves Hyperglycemia in Diabetic Mice.

The hypoglycemic effect of the compound has been examined in two spontaneous animal models of diabetes (ob/ob and db/db mice). The ob/ob mice lacks leptin gene and is also considered a typical model for obesity. The db/db mice have defective leptin receptor and show hyperglycemia with significant weight gain. The compound at a dose of 5, 10 and 50 mg/kg body weight was given orally in these animals for a period of 15–21 days. Treatment of both ob/ob and db/db diabetic animals resulted in significant improvement of hyperglycemic conditions. Results are essentially the same for compound 1.

FIG. 7. The Compounds 1 and 2 in Example 1 Reduce Body Weight Gain in Animal Model of Obesity.

The leptin knock-out mice (ob/ob) are considered a suitable model for obesity besides diabetes. In order to test the efficacy of these compounds towards obesity, ob/ob mice were treated with compound for 21 days. As shown in FIG. 7, single dose daily treatment of ob/ob mice with compound can result in 35% improvement in body weight gain, indicating the utility of these compounds for the treatment of obesity. This finding is opposite from that using other thiazolidines, which typically increase weight.

FIG. 8. The Compound 2 in Example 1 Can Improve Insulin Resistance and Lipid Homeostasis.

The leptin knock-out ob/ob mice is also considered a good model for insulin resistance. Treatment of these animals with the compound 2 lowered serum insulin concentration by >70%. Similarly, a 48% decrease in triglyceride level and >50% decrease in serum cholesterol concentrations were observed in 15-day treatment study. These results indicate that the compounds have strong anti-lipidemic properties and can improve the sensitivity of insulin.

In a separate study, surprisingly it was observed that these compounds are non-adipogenic in contrast to other known thiazolidinediones and has very weak or no affinity towards peroxisome proliferator activator receptor-gamma (PPAR-γ). All of these biological findings suggest the compounds have novel properties and work by a very different mechanism of action from PPAR-γ binding.

FIG. 9. Known PPAR-g Agonist Rosiglitazone is an Adipogenic Agent, but Compound 2 is not.

Human subcutaneous preadipocytes were cultured in 96 well plate in presence of vehicle or different doses (0.01, 0.1, 1.0, and 10 microMolar) of either rosiglitazone (BRL) or compound 2 (BLX) for 13 days. Every 72 hours media were changed with fresh compound. As TNF inhibits adipogenesis process, it was kept as negative control of the experiment where coincubation with rosiglitazone showed a significant reduction in adipogenesis compared to rosiglitazone alone. On day 13 cells were fixed and lipid (triglycerides) accumulation was measured by staining with Oil Red O and pictures were under the microscope. To have more quantitative data, Oil Red O was extracted by adding isopropanol and measured spectrophotometrically at 540 nM (as shown in the bar graph). It can be seen that regardless of dosage, compound 2 did not cause accumulation of lipids. Rosiglitazone showed a dose dependent increase in lipid production, which could be inhibited by addition of TNFα.

What is claimed is:

1. A compound formula (I)

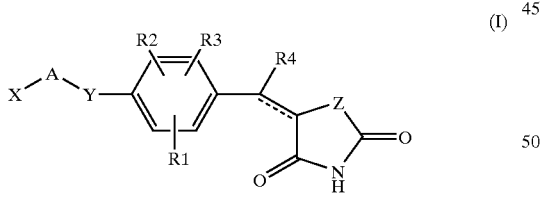

(I)

its tautomeric forms, its stereoisomers, its polymorphs, its pharmaceutically acceptable salts, its pharmaceutically acceptable solvates, wherein - - - represents an optional double bond; Y represents oxygen, sulfur or NR, wherein R represents hydrogen or alkyl; Z represents oxygen or sulfur; $R_1$, $R_2$, $R_3$ and $R_4$ may be same or different and independently represent hydrogen, halogen, hydroxy, nitro, cyano, formyl, amino, alkyl, or alkoxy; A represents a bond or substituted or unsubstituted aryl, heterocyclyl or heteroaryl ring; X represents an alpha amino carboxylic acid or alpha amino carboxylic acid derivative bonded to A or Y through its alpha side chain.

2. A compound of formula (I) according to claim 1, wherein the X-A-Y-represents an amino acid selected from the group consisting of substituted or unsubstituted arginine, asparagine, cysteine, glutamine, histidine, lysine, methionine, ornithine, proline, serine, threonine, tryptophan, tyrosine and their derivatives.

3. A compound according to claim 1 wherein A represents a substituted or unsubstituted alkyl, heterocyclyl or heteroaryl ring.

4. A compound according to claim 1 wherein X-A-represents an amino acid selected from the group consisting of alanine, glycine, isoleucine and leucine and their derivatives.

5. A compound according to claim 1 wherein A represents a bond.

6. A compound according to any of claims 1 through 5 wherein Z is sulfur and Y is oxygen.

7. A compound according to any of claims 1 through 5 wherein $R_1$ through $R_4$ are hydrogen.

8. A compound according to any of claims 1 through 5 wherein the - - - double bond is present.

9. A compound according to any of claims 1 through 5 wherein the - - - double bond is absent.

10. A compound according to claim 2 wherein X-A-Y- comprises tyrosine.

11. A compound according to claim 2 wherein X-A-Y comprises a tyrosine derivative.

12. A compound according to claim 11 wherein said derivative comprises an alkyl ester of tyrosine.

13. A compound according to claim 12 wherein said ester is the methyl ester.

14. A compound according to claim 10 or 11 wherein $R_1$, $R_2$, $R_3$ and $R_4$ are hydrogen and Z is sulfur.

15. A compound according to claim 14 wherein the - - - double bond is present.

16. A compound according to claim 14 wherein the - - - double bond is absent.

17. A compound according to claim 1, which is selected from the group consisting of:

5-[4-(4-(2-Amino-2-carboxyethyl)phenoxy)benzilidene]thiazolidin-2,4-dione or its salts;

5-[4-(4-(2-Amino-2-methoxycarbonylethyl)phenoxy)benzilidene]thiazolidin-2,4-dione or its salts;

5-[4-(4-(2-Amino-2-carboxyethyl)phenoxy)benzyl]thiazolidin-2,4-dione or its salts;

5-[4-(4-(2-Amino-2-methoxycarbonylethyl)phenoxy)benzyl]thiazolidin-2,4-dione or its salts;

5-[4-(4-(2-Amino-2-carboxyethyl)phenoxy)benzilidene]oxazolidin-2,4-dione or its salts;

5-[4-(4-(2-Amino-2-methoxycarbonylethyl)phenoxy)benzilidene]oxazolidin-2,4-dione or its salts;

5-[4-(4-(2-Amino-2-carboxyethyl)phenoxy)benzyl]oxazolidin-2,4-dione or its salts;

5-[4-(4-(2-Amino-2-methoxycarbonylethyl)phenoxy)benzyl]oxazolidin-2,4-dione or its salts;

5-[4-(4-(2-Amino-2-carboxyethyl)phenoxy)-2,6-difluorobenzilidene]oxazolidin-2,4-dione or its salts;

5-[4-(4-(2-Amino-2-methoxycarbonylethyl)phenoxy)-2,6-difluorobenzilidene]oxazolidin-2,4-dione or its salts;

5-[4-(4-(2-Amino-2-carboxyethyl)phenoxy)-2,6-difluorobenzyl]oxazolidin-2,4-dione or its salts;

5-[4-(4-(2-Amino-2-methoxycarbonylethyl)phenoxy)-2,6-difluorobenzyl]oxazolidin-2,4-dione or its salts;

5-[4-(4-(2-Amino-2-carboxyethyl)phenoxy)-2,6-difluorobenzilidene]thiazolidin-2,4-dione or its salts;

5-[4-(4-(2-Amino-2-methoxycarbonylethyl)phenoxy)-2,6-difluorobenzilidene]thiazolidin-2,4-dione or its salts;

5-[4-(4-(2-Amino-2-carboxyethyl)phenoxy)-2,6-difluorobenzyl]thiazolidin-2,4-dione or its salts;

5-[4-(4-(2-Amino-2-methoxycarbonylethyl)phenoxy)-2,6-difluorobenzyl]thiazolidin-2,4-dione or its salts;

5-[4-(4-(2-Amino-2-carboxyethyl)phenoxy)-2,3-difluorobenzilidene]thiazolidin-2,4-dione or its salts;

5-[4-(4-(2-Amino-2-methoxycarbonylethyl)phenoxy)-2,3-difluorobenzilidene]thiazolidin-2,4-dione or its salts;

5-[4-(4-(2-Amino-2-carboxyethyl)phenoxy)-2,3-difluorobenzyl]thiazolidin-2,4-dione or its salts;

5-[4-(4-(2-Amino-2-methoxycarbonylethyl)phenoxy)-2,3-difluorobenzyl]thiazolidin-2,4-dione or its salts;

5-[4-(4-(2-Amino-2-carboxyethyl)phenoxy)-2,3-difluorobenzilidene]oxazolidin-2,4-dione or its salts;

5-[4-(4-(2-Amino-2-methoxycarbonylethyl)phenoxy)-2,3-difluorobenzilidene]oxazolidin-2,4-dione or its salts;

5-[4-(4-(2-Amino-2-carboxyethyl)phenoxy)-2,3-difluorobenzyl]oxazolidin-2,4-dione or its salts;

5-[4-(4-(2-Amino-2-methoxycarbonylethyl)phenoxy)-2,3-difluorobenzyl]oxazolidin-2,4-dione or its salts;

5-[4-(4-(2-Amino-2-carboxyethyl)phenoxy)-3-methylbenzilidene]oxazolidin-2,4-dione or its salts;

5-[4-(4-(2-Amino-2-methoxycarbonylethyl)phenoxy)-3-methylbenzilidene]oxazolidin-2,4-dione or its salts;

5-[4-(4-(2-Amino-2-carboxyethyl)phenoxy)-3-methylbenzyl]oxazolidin-2,4-dione or its salts;

5-[4-(4-(2-Amino-2-methoxycarbonylethyl)phenoxy)-3-methylbenzyl]oxazolidin-2,4-dione or its salts;

5-[4-(4-(2-Amino-2-carboxyethyl)phenoxy)-3-methylbenzilidene]thiazolidin-2,4-dione or its salts;

5-[4-(4-(2-Amino-2-methoxycarbonylethyl)phenoxy)-3-methylbenzilidene]thiazolidin-2,4-dione or its salts;

5-[4-(4-(2-Amino-2-carboxyethyl)phenoxy)-3-methylbenzyl]thiazolidin-2,4-dione or its salts;

5-[4-(4-(2-Amino-2-methoxycarbonylethyl)phenoxy)-3-methylbenzyl]thiazolidin-2,4-dione or its salts;

5-[4-(4-(2-Amino-2-carboxyethyl)phenoxy)-3-nitrobenzilidene]thiazolidin-2,4-dione or its salts;

5-[4-(4-(2-Amino-2-methoxycarbonylethyl)phenoxy)-3-nitrobenzilidene]thiazolidin-2,4-dione or its salts;

5-[4-(4-(2-Amino-2-carboxyethyl)phenoxy)-3-nitrobenzyl]thiazolidin-2,4-dione or its salts;

5-[4-(4-(2-Amino-2-methoxycarbonylethyl)phenoxy)-3-nitrobenzyl]thiazolidin-2,4-dione or its salts;

5-[4-(4-(2-Amino-2-carboxyethyl)phenoxy)-3-nitrobenzilidene]oxazolidin-2,4-dione or its salts;

5-[4-(4-(2-Amino-2-methoxycarbonylethyl)phenoxy)-3-nitrobenzilidene]oxazolidin-2,4-dione or its salts;

5-[4-(4-(2-Amino-2-carboxyethyl)phenoxy)-3-nitrobenzyl]oxazolidin-2,4-dione or its salts;

5-[4-(4-(2-Amino-2-methoxycarbonylethyl)phenoxy)-3-nitrobenzyl]oxazolidin-2,4-dione or its salts;

5-[4-(4-(2-Amino-2-carboxyethyl)phenoxy)-3-aminobenzilidene]thiazolidin-2,4-dione or its salts;

5-[4-(4-(2-Amino-2-methoxycarbonylethyl)phenoxy)-3-aminobenzilidene]thiazolidin-2,4-dione or its salts;

5-[4-(4-(2-Amino-2-carboxyethyl)phenoxy)-3-aminobenzyl]thiazolidin-2,4-dione or its salts;

5-[4-(4-(2-Amino-2-methoxycarbonylethyl)phenoxy)-3-aminobenzyl]thiazolidin-2,4-dione or its salts;

5-[4-(4-(2-Amino-2-carboxyethyl)phenoxy)-3-aminobenzilidene]oxazolidin-2,4-dione or its salts;

5-[4-(4-(2-Amino-2-methoxycarbonylethyl)phenoxy)-3-aminobenzilidene]oxazolidin-2,4-dione or its salts;

5-[4-(4-(2-Amino-2-carboxyethyl)phenoxy)-3-aminobenzyl]oxazolidin-2,4-dione or its salts;

5-[4-(4-(2-Amino-2-methoxycarbonylethyl)phenoxy)-3-aminobenzyl]oxazolidin-2,4-dione or its salts;

5-[4-(4-(2-Amino-2-carboxyethyl)phenoxy)-2-fluorobenzilidene]thiazolidin-2,4-dione or its salts;

5-[4-(4-(2-Amino-2-methoxycarbonylethyl)phenoxy)-2-fluorobenzilidene]thiazolidin-2,4-dione or its salts;

5-[4-(4-(2-Amino-2-carboxyethyl)phenoxy)-2-fluorobenzyl]thiazolidin-2,4-dione or its salts;

5-[4-(4-(2-Amino-2-methoxycarbonylethyl)phenoxy)-2-fluorobenzyl]thiazolidin-2,4-dione or its salts;

5-[4-(4-(2-Amino-2-carboxyethyl)phenoxy)-2-fluorobenzilidene]oxazolidin-2,4-dione or its salts;

5-[4-(4-(2-Amino-2-methoxycarbonylethyl)phenoxy)-2-fluorobenzilidene]oxazolidin-2,4-dione or its salts;

5-[4-(4-(2-Amino-2-carboxyethyl)phenoxy)-2-fluorobenzyl]oxazolidin-2,4-dione or its salts;

5-[4-(4-(2-Amino-2-methoxycarbonylethyl)phenoxy)-2-fluorobenzyl]oxazolidin-2,4-dione or its salts;

5-[4-(4-(2-Amino-2-carboxyethyl)phenoxy)-3-fluorobenzilidene]thiazolidin-2,4-dione or its salts;

5-[4-(4-(2-Amino-2-methoxycarbonylethyl)phenoxy)-3-fluorobenzilidene]thiazolidin-2,4-dione or its salts;

5-[4-(4-(2-Amino-2-carboxyethyl)phenoxy)-3-fluorobenzyl]thiazolidin-2,4-dione or its salts;

5-[4-(4-(2-Amino-2-methoxycarbonylethyl)phenoxy)-3-fluorobenzyl]thiazolidin-2,4-dione or its salts;

5-[4-(4-(2-Amino-2-carboxyethyl)phenoxy)-3-fluorobenzilidene]oxazolidin-2,4-dione or its salts;

5-[4-(4-(2-Amino-2-methoxycarbonylethyl)phenoxy)-3-fluorobenzilidene]oxazolidin-2,4-dione or its salts;

5-[4-(4-(2-Amino-2-carboxyethyl)phenoxy)-3-fluorobenzyl]oxazolidin-2,4-dione or its salts;

5-[4-(4-(2-Amino-2-methoxycarbonylethyl)phenoxy)-3-fluorobenzyl]oxazolidin-2,4-dione or its salts;

5-[4-(4-(2-Amino-2-carboxyethyl)phenoxy)-2-trifluoromethylbenzilidene]thiazolidin-2,4-dione or its salts;

5-[4-(4-(2-Amino-2-methoxycarbonylethyl)phenoxy)-2-trifluoromethylbenzilidene]thiazolidin-2,4-dione or its salts;

5-[4-(4-(2-Amino-2-carboxyethyl)phenoxy)-2-trifluoromethylbenzyl]thiazolidin-2,4-dione or its salts;

5-[4-(4-(2-Amino-2-methoxycarbonylethyl)phenoxy)-2-trifluoromethylbenzyl]thiazolidin-2,4-dione or its salts;

5-[4-(4-(2-Amino-2carboxyethyl)phenoxy)-2-trifluoromethylbenzilidene]oxazolidin-2,4-dione or its salts;

5-[4-(4-(2-Amino-2-methoxycarbonylethyl)phenoxy)-2-trifluoromethylbenzilidene]oxazolidin-2,4-dione or its salts;

5-[4-(4-(2-Amino-2-carboxyethyl)phenoxy)-2-trifluoromethylbenzyl]oxazolidin-2,4-dione or its salts;

5-[4-(4-(2-Amino-2-methoxycarbonylethyl)phenoxy)-2-trifluoromethylbenzyl]oxazolidin-2,4-dione or its salts;

5-[4-(4-(2-Amino-2-carboxyethyl)phenoxy)-3-trifluoromethylbenzilidene]thiazolidin-2,4-dione or its salts;

5-[4-(4-(2-Amino2-methoxycarbonylethyl)phenoxy)-3-trifluoromethylbenzilidene]thiazolidin-2,4-dione or its salts;

5-[4-(4-(2-Amino-2-carboxyethyl)phenoxy)-3-trifluoromethylbenzyl]thiazolidin-2,4-dione or its salts;
5-[4-(4-(2-Amino-2-methoxycarbonylethyl)phenoxy)-3-trifluoromethylbenzyl]thiazolidin-2,4-dione or its salts;
5-[4-(4-(2-Amino-2-carboxyethyl)phenoxy)-3-trifluoromethylbenzilidene]oxazolidin-2,4-dione or its salts;
5-[4-(4-(2-Amino-2-methoxycarbonylethyl)phenoxy)-3-trifluoromethylbenzilidene]oxazolidin-2,4-dione or its salts;
5-[4-(4-(2-Amino-2-carboxyethyl)phenoxy)-3-trifluoromethylbenzyl]oxazolidin-2,4-dione or its salts;
5-[4-(4-(2-Amino-2-methoxycarbonylethyl)phenoxy)-3-trifluoromethylbenzyl]oxazolidin-2,4-dione or its salts;
5-[4-(4-(2-Amino-2-carboxyethyl)-2,6-difluorophenoxy)benzilidene]oxazolidin-2,4-dione or its salts;
5-[4-(4-(2-Amino-2-methoxycarbonylethyl)-2,6-difluorophenoxy)benzilidene]oxazolidin-2,4-dione or its salts
5-[4-(4-(2-Amino-2-carboxyethyl)-2,6-difluorophenoxy)benzyl]oxazolidin-2,4-dione or its salts;
5-[4-(4-(2-Amino-2-methoxycarbonylethyl)-2,6-difluorophenoxy)benzyl]oxazolidin-2,4-dione or its salts;
5-[4-(4-(2-Amino-2-carboxyethyl)-2,6-difluorophenoxy)benzilidene]thiazolidin-2,4-dione or its salts;
5-[4-(4-(2-Amino-2-methoxycarbonylethyl)-2,6-difluorophenoxy)benzilidene]thiazolidin-2,4-dione or its salts;
5-[4-(4-(2-Amino-2-carboxyethyl)-2,6-difluorophenoxy)benzyl]thiazolidin-2,4-dione or its salts;
5-[4-(4-(2-Amino-2-methoxycarbonylethyl)-2,6-difluorophenoxy)benzyl]thiazolidin-2,4-dione or its salts;
5-[4-(4-(2-Amino-2-carboxyethyl)-2,3-difluorophenoxy)benzilidene]thiazolidin-2,4-dione or its salts
5-[4-(4-(2-Amino-2-methoxycarbonylethyl)-2,3-difluorophenoxy)benzilidene]thiazolidin-2,4-dione or its salts;
5-[4-(4-(2-Amino-2-carboxyethyl)-2,3-difluorophenoxy)benzyl]thiazolidin-2,4-dione or its salts;
5-[4-(4-(2-Amino-2-methoxycarbonylethyl)-2,3-difluorophenoxy)benzyl]thiazolidin-2,4-dione or its salts;
5-[4-(4-(2-Amino-2-carboxyethyl)-2,3-difluorophenoxy)benzilidene]oxazolidin-2,4-dione or its salts;
5-[4-(4-(2-Amino-2-methoxycarbonylethyl)-2,3-difluorophenoxy)benzilidene]oxazolidin-2,4-dione or its salts;
5-[4-(4-(2-Amino-2-carboxyethyl)-2,3-difluorophenoxy)benzyl]oxazolidin-2,4-dione or its salts;
5-[4-(4-(2-Amino-2-methoxycarbonylethyl)-2,3-difluorophenoxy)benzyl]oxazolidin-2,4-dione or its salts;
5-[4-(4-(2-Amino-2-carboxyethyl)-3-methylphenoxy)benzilidene]oxazolidin-2,4-dione or its salts;
5-[4-(4-(2-Amino-2-methoxycarbonylethyl)-3-methylphenoxy)benzilidene]oxazolidin-2,4-dione or its salts;
5-[4-(4-(2-Amino-2-carboxyethyl)-3-methylphenoxy)benzyl]oxazolidin-2,4-dione or its salts;
5-[4-(4-(2-Amino-2-methoxycarbonylethyl)-3-methylphenoxy)benzyl]oxazolidin-2,4-dione or its salts;
5-[4-(4-(2-Amino-2-carboxyethyl)-3-methylphenoxy)benzilidene]thiazolidin-2,4-dione or its salts;
5-[4-(4-(2-Amino-2-methoxycarbonylethyl)-3-methylphenoxy)benzilidene]thiazolidin-2,4-dione or its salts;
5-[4-(4-(2-Amino-2-carboxyethyl)-3-methylphenoxy)benzyl]thiazolidin-2,4-dione or its salts;
5-[4-(4-(2-Amino-2-methoxycarbonylethyl)-3-methylphenoxy)benzyl]thiazolidin-2,4-dione or its salts;
5-[4-(4-(2-Amino-2-carboxyethyl)-3-nitrophenoxy)benzilidene]thiazolidin-2,4-dione or its salts;
5-[4-(4-(2-Amino-2-methoxycarbonylethyl)-3-nitrophenoxy)benzilidene]thiazolidin-2,4-dione or its salts;
5-[4-(4-(2-Amino-2-carboxyethyl)-3-nitrophenoxy)benzyl]thiazolidin-2,4-dione or its salts;
5-[4-(4-(2-Amino-2-methoxycarbonylethyl)-3-nitrophenoxy)benzyl]thiazolidin-2,4-dione or its salts;
5-[4-(4-(2-Amino-2-carboxyethyl)-3-nitrophenoxy)benzilidene]oxazolidin-2,4-dione or its salts;
5-[4-(4-(2-Amino-2-methoxycarbonylethyl)-3-nitrophenoxy)benzilidene]oxazolidin-2,4-dione or its salts;
5-[4-(4-(2-Amino-2-carboxyethyl)-3-nitrophenoxy)benzyl]oxazolidin-2,4-dione or its salts;
5-[4-(4-(2-Amino-2-methoxycarbonylethyl)-3-nitrophenoxy)benzyl]oxazolidin-2,4-dione or its salts;
5-[4-(4-(2-Amino-2-carboxyethyl)-3-aminophenoxy)benzilidene]thiazolidin-2,4-dione or its salts;
5-[4-(4-(2-Amino-2-methoxycarbonylethyl)-3-aminophenoxy)benzilidene]thiazolidin-2,4-dione or its salts;
5-[4-(4-(2-Amino-2-carboxyethyl)-3-aminophenoxy)benzyl]thiazolidin-2,4-dione or its salts;
5-[4-(4-(2-Amino-2-methoxycarbonylethyl)-3-aminophenoxy)benzyl]thiazolidin-2,4-dione or its salts;
5-[4-(4-(2-Amino-2-carboxyethyl)-3-aminophenoxy)benzilidene]oxazolidin-2,4-dione or its salts;
5-[4-(4-(2-Amino-2-methoxycarbonylethyl)-3-aminophenoxy)benzilidene]oxazolidin-2,4-dione or its salts;
5-[4-(4-(2-Amino-2-carboxyethyl)-3-aminophenoxy)benzyl]oxazolidin-2,4-dione or its salts;
5-[4-(4-(2-Amino-2-methoxycarbonylethyl)-3-aminophenoxy)benzyl]oxazolidin-2,4-dione or its salts;
5-[4-(4-(2-Amino-2-carboxyethyl)-2-fluorophenoxy)benzilidene]thiazolidin-2,4-dione or its salts;
5-[4-(4-(2-Amino-2-methoxycarbonylethyl)-2-fluorophenoxy)benzilidene]thiazolidin-2,4-dione or its salts;
5-[4-(4-(2-Amino-2-carboxyethyl)-2-fluorophenoxy)benzyl]thiazolidin-2,4-dione or its salts;
5-[4-(4-(2-Amino-2-methoxycarbonylethyl)-2-fluorophenoxy)benzyl]thiazolidin-2,4-dione or its salts;
5-[4-(4-(2-Amino-2-carboxyethyl)-2-fluorophenoxy)benzilidene]oxazolidin-2,4-dione or its salts;
5-[4-(4-(2-Amino-2-methoxycarbonylethyl)-2-fluorophenoxy)benzilidene]oxazolidin-2,4-dione or its salts;

5-[4-(4-(2-Amino-2-carboxyethyl)-2-fluorophenoxy) benzyl]oxazolidin-2,4-dione or its salts;

5-[4-(4-(2-Amino-2-methoxycarbonylethyl)-2-fluorophenoxy)benzyl]oxazolidin-2,4-dione or its salts;

5-[4-(4-(2-Amino-2-carboxyethyl)-3-fluorophenoxy) benzilidene]thiazolidin-2,4-dione or its salts;

5-[4-(4-(2-Amino-2-methoxycarbonylethyl)-3-fluorophenoxy)benzilidene]thiazolidin-2,4-dione or its salts;

5-[4-(4-(2-Amino-2-carboxyethyl)-3-fluorophenoxy) benzyl]thiazolidin-2,4-dione or its salts;

5-[4-(4-(2-Amino-2-methoxycarbonylethyl)-3-fluorophenoxy)benzyl]thiazolidin-2,4-dione or its salts;

5-[4-(4-(2-Amino-2-carboxyethyl)-3-fluorophenoxy) benzilidene]oxazolidin-2,4-dione or its salts;

5-[4-(4-(2-Amino-2-methoxycarbonylethyl)-3-fluorophenoxy)benzilidene]oxazolidin-2,4-dione or its salts;

5-[4-(4-(2-Amino-2-carboxyethyl)-3-fluorophenoxy) benzyl]oxazolidin-2,4-dione or its salts;

5-[4-(4-(2-Amino-2-methoxycarbonylethyl)-3-fluorophenoxy)benzyl]oxazolidin-2,4-dione or its salts;

5-[4-(4-(2-Amino-2-carboxyethyl)-2-trifluoromethylphenoxy)benzilidene]thiazolidin-2,4-dione or its salts;

5-[4-(4-(2-Amino-2-methoxycarbonylethyl)-2-trifluoromethylphenoxy)benzilidene]thiazolidin-2,4-dione or its salts;

5-[4-(4-(2-Amino-2-carboxyethyl)-2-trifluoromethylphenoxy)benzyl]thiazolidin-2,4-dione or its salts;

5-[4-(4-(2-Amino-2-methoxycarbonylethyl)-2-trifluoromethylphenoxy)benzyl]thiazolidin-2,4-dione or its salts;

5-[4-(4-(2-Amino-2-carboxyethyl)-2-trifluoromethylphenoxy)benzilidene]oxazolidin-2,4-dione or its salts;

5-[4-(4-(2-Amino-2-methoxycarbonylethyl)-2-trifluoromethylphenoxy)benzilidene]oxazolidin-2,4-dione or its salts;

5-[4-(4-(2-Amino-2-carboxyethyl)-2-trifluoromethylphenoxy)benzyl]oxazolidin-2,4-dione or its salts;

5-[4-(4-(2-Amino-2-methoxycarbonylethyl)-2-trifluoromethylphenoxy)benzyl]oxazolidin-2,4-dione or its salts;

5-[4-(4-(2-Amino-2-carboxyethyl)-3-trifluoromethylphenoxy)benzilidene]thiazolidin-2,4-dione or its salts;

5-[4-(4-(2-Amino-2-methoxycarbonylethyl)-3-trifluoromethylphenoxy)benzilidene]thiazolidin-2,4-dione or its salts;

5-[4-(4-(2-Amino-2-carboxyethyl)-3-trifluoromethylphenoxy)benzyl]thiazolidin-2,4-dione or its salts;

5-[4-(4-(2-Amino-2-methoxycarbonylethyl)-3-trifluoromethylphenoxy)benzyl]thiazolidin-2,4-dione or its salts;

5-[4-(4-(2-Amino-2-carboxyethyl)-3-trifluoromethylphenoxy)benzilidene]oxazolidin-2,4-dione or its salts;

5-[4-(4-(2-Amino-2-methoxycarbonylethyl)-3-trifluoromethylphenoxy)benzilidene]oxazolidin-2,4-dione or its salts;

5-[4-(4-(2-Amino-2-carboxyethyl)-3-trifluoromethylphenoxy)benzyl]oxazolidin-2,4-dione or its salts;

5-[4-(4-(2-Amino-2-methoxycarbonylethyl)-3-trifluoromethylphenoxy)benzyl]oxazolidin-2,4-dione or its salts;

5-[4-(4-(2-t-butoxycarbonylamino-2-methoxycarbonylethyl)phenoxy)benzilidene]thiazolidin-2,4-dione or its salts;

5-[4-(4-(2-t-butoxycarbonylamino-2-methoxycarbonylethyl)phenoxy)benzyl]thiazolidin-2,4-dione or its salts;

5-[4-(4-(2-t-butoxycarbonylamino-2-methoxycarbonylethyl)phenoxy)benzilidene]oxazolidin-2,4-dione or its salts;

5-[4-(4-(2-t-butoxycarbonylamino-2-methoxycarbonylethyl)phenoxy)benzyl]oxazolidin-2,4-dione or its salts.

5-[4-(4-(2-t-butoxycarbonylamino-2-carboxyethyl) phenoxy)benzilidene]thiazolidin-2,4-dione or its salts;

5-[4-(4-(2-t-butoxycarbonylamino-2-carboxyethyl) phenoxy)benzyl]thiazolidin-2,4-dione or its salts;

5-[4-(4-(2-t-butoxycarbonylamino-2-carboxyethyl) phenoxy)benzilidene]oxazolidin-2,4-dione or its salts and 5-[4-(4-(2-t-butoxycarbonylamino-2-carboxyethyl) phenoxy)benzyl]oxazolidin-2,4-dione or its salts.

18. A process for the preparation of an amino acid phenyl ether of formula (I)

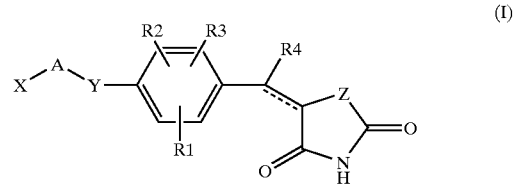

(I)

its derivatives, its analogs, its tautomeric forms, its stereoisomers, its polymorphs, its pharmaceutically acceptable salts, its pharmaceutically acceptable solvates, wherein - - - represents a bond; Y represents oxygen, sulfur or NR, wherein R represents hydrogen or alkyl; Z represents oxygen or sulfur; $R_1$, $R_2$, $R_3$ and $R_4$ may be same or different and independently represent hydrogen, halogen, hydroxy, nitro, cyano, formyl, amino, alkyl, or alkoxy; A represents a bond or substituted or unsubstituted aryl, heterocyclyl or heteroaryl ring; X represents an alpha amino carboxylic acid or its derivatives bonded to A or Y through its alpha side chain, which comprises i). reacting the compound of formula (IIIa)

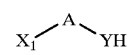

(IIIa)

which represents a protected amino acid and all other symbols are as defined above with the compound of formula (IIIb)

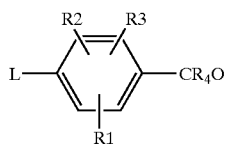

(IIIb)

wherein L represents a nucleophilic aromatic substitution leaving group, $R_1$, $R_2$ and $R_3$ are as defined above to produce a compound of formula (IIIc)

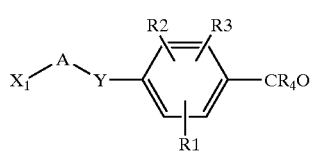

(IIIc)

ii). reacting the compound of the formula (IIIc) with 2,4-thiazolidinedione or 2,4-oxazolidinedione to yield a compound of formula (IIId) and

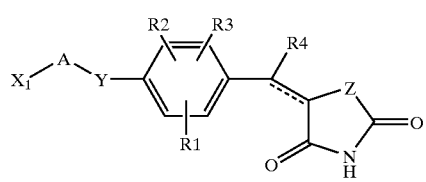

(IIId)

iii). deprotecting the amino acid group of formula (IIId) to yield compound of formula (I).

19. A process for the preparation of amino acid phenyl ethers of formula (I)

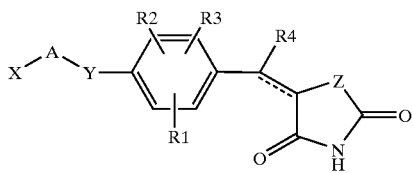

(I)

their derivatives, their analogs, their tautomeric forms, their stereoisomers, their polymorphs, their pharmaceutically acceptable salts, their pharmaceutically acceptable solvates, wherein - - - represents no bond; Y represents oxygen, sulfur or NR, wherein R represents hydrogen or alkyl; Z represents sulfur; $R_1$, $R_2$, $R_3$ and $R_4$ may be same or different and independently represent hydrogen, halogen, hydroxy, nitro, cyano, formyl, amino, alkyl, or alkoxy; A represents a bond or substituted or unsubstituted aryl, heterocyclyl or heteroaryl ring; X represents an alpha amino carboxylic acid or its derivatives bonded to A or Y through its alpha side chain, by reacting the compound of formula (IIIe)

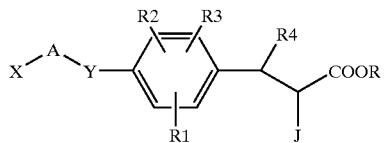

(IIIe)

wherein J is halogen atom and R is a lower alkyl group with thiourea followed by treatment with an acid.

20. A process for the preparation of an amino acid phenyl ether of formula (I)

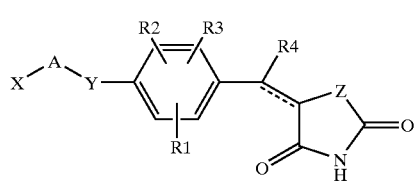

(I)

its derivatives, its analogs, its tautomeric forms, its stereoisomers, its polymorphs, its pharmaceutically acceptable salts, its pharmaceutically acceptable solvates, wherein - - - represents a bond; Y represents oxygen, sulfur or NR, wherein R represents hydrogen or alkyl; Z represents oxygen or sulfur; $R_1$, $R_2$, $R_3$ and $R_4$ may be same or different and independently represent hydrogen, halogen, hydroxy, nitro, cyano, formyl, amino, alkyl, or alkoxy; A represents a bond or substituted or unsubstituted aryl, heterocyclyl or heteroaryl ring; X represents an alpha amino carboxylic acid or its derivatives bonded to A through its alpha side chain, by reacting a compound of formula (IIIf)

(IIIf)

wherein L is a nucleophilic leaving group with a compound of the formula (IIIg).

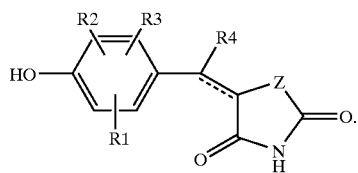

(IIIg)

21. A process for the preparation of an amino acid phenyl ether of formula (I)

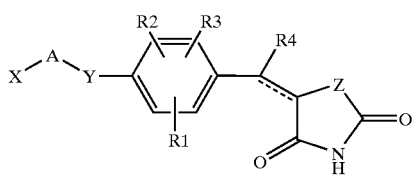

(I)

its derivatives, its analogs, its tautomeric forms, its stereoisomers, its polymorphs, its pharmaceutically acceptable salts, its pharmaceutically acceptable solvates, wherein - - - represents a bond; Y represents oxygen, sulfur or NR, wherein R represents hydrogen or alkyl; Z represents oxygen or sulfur; $R_1$, $R_2$, $R_3$ and $R_4$ may be same or different and independently represent hydrogen, halogen, hydroxy, nitro, cyano, formyl, amino, alkyl, or alkoxy; A represents a bond or substituted or unsubstituted aryl, heterocyclyl or heteroaryl ring; X represents an alpha amino carboxylic acid or its derivatives bonded to A through its alpha side chain, by reacting a compound of formula (IIIh)

(IIIh)

where A and X are as defined above with a compound of the formula (IIIg)

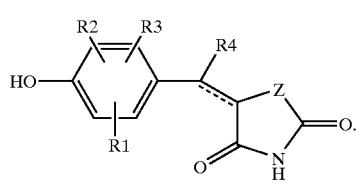

(IIIg)

22. A process for the preparation of compound of formula (I)

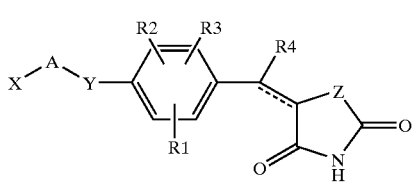

(I)

wherein "- - -" represents no bond by reducing compounds of formula (I) wherein "- - -" represents a bond and all other symbols are as defined in claim 1.

23. A pharmaceutical composition, which comprises a pharmaceutically effective amount of an amino acid phenyl ether of formula (I)

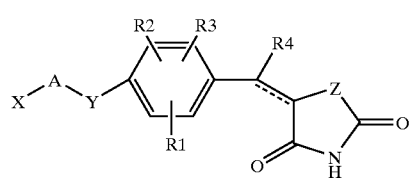

(I)

as defined in claim 1 and a pharmaceutically acceptable carrier, diluent, excipient or solvate.

24. A method for reducing glucose in plasma comprising administering an effective amount of a compound of formula (I) as defined in claim 1 to a patient in need thereof.

25. A method for reducing free fatty acids in plasma comprising administering an effective amount of a compound of formula (I) as defined in claim 1 to a patient in need thereof.

26. A method for reducing cholesterol in plasma comprising administering an effective amount of a compound of formula (I) as defined in claim 1 to a patient in need thereof.

27. A method for reducing triglyceride levels in plasma comprising administering an effective amount of a compound of formula (I) as defined in claim 1 to a patient in need thereof.

28. A method for treating obesity comprising administering an effective amount of a compound of formula (I) as defined in claim 1 to a patient in need thereof.

29. A method for treating autoimmune diseases comprising administering an effective amount of a compound of formula (I) as defined in claim 1 to a patient in need thereof.

30. A method for treating inflammation comprising administering an effective amount of a compound of formula (I) as defined in claim 1 to a patient in need thereof.

31. A method for treating immunological disease comprising administering an effective amount of a compound of formula (I) as defined in claim 1 to a patient in need thereof.

32. A method according to claim 29, wherein the autoimmune disease is multiple sclerosis.

33. A method according to claim 29, wherein the autoimmune disease is rheumatoid arthritis.

34. A method according to claim 30, wherein the inflammation is mediated by cyclooxygenase.

35. A method according to claim 31, wherein the immunological diseases is mediated by cytokines.

36. A method for treating a disorder associated with insulin resistance comprising administering an effective amount of a compound of formula (I) as defined in claim 1 to a patient in need thereof.

37. An intermediate of formula (IIIc)

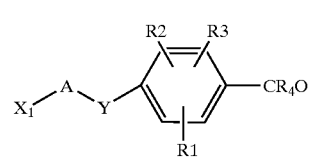

(IIIc)

its derivatives, its analogs, its tautomeric forms, its stereoisomers, its polymorphs, its pharmaceutically acceptable salts, their pharmaceutically acceptable solvates, wherein Y represents oxygen, sulfur or NR, wherein R represents hydrogen or alkyl; $R_1$, $R_2$, $R_3$ and $R_4$ may be same or different and independently represent hydrogen, halogen, hydroxy, nitro, cyano, formyl, amino, alkyl, or alkoxy; A represents substituted or unsubstituted aryl; X represents an alpha amino carboxylic acid or its derivatives bonded to A through its alpha amino side chain.

38. An intermediate of formula (IIIc)

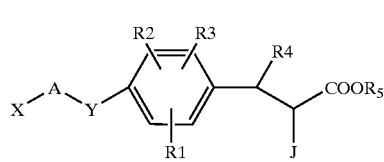

(IIIe)

its derivatives, its analogs, its tautomeric forms, its stereoisomers, its polymorphs, its pharmaceutically acceptable salts, its pharmaceutically acceptable solvates, wherein Y represents oxygen, sulfur or NR, wherein R represents hydrogen or alkyl; $R_1$, $R_2$, $R_3$ and $R_4$ may be same or different and independently represent hydrogen, halogen, hydroxy, nitro, cyano, formyl, amino, alkyl, or alkoxy; A represents substituted or unsubstituted aryl; X represents an alpha amino carboxylic acid or its derivatives bonded to A through its alpha amino side chain; J represents halogen atom and $R_5$ represents lower alkyl group.

39. The compound as claimed in claim 1, wherein said pharmaceutically acceptable salt is selected from hydrochloride, hydrobromide, sodium, potassium or magnesium salt.

* * * * *